United States Patent
Franke et al.

(10) Patent No.: US 9,018,420 B2
(45) Date of Patent: Apr. 28, 2015

(54) USE OF SUPPORTED IONIC LIQUID PHASE (SILP) CATALYST SYSTEMS IN THE HYDROFORMYLATION OF OLEFIN-CONTAINING MIXTURES TO ALDEHYDE MIXTURES WITH A HIGH CONTENT OF ALDEHYDES UNBRANCHED IN THE 2 POSITION

(75) Inventors: Robert Franke, Marl (DE); Nicole Brausch, Essen (DE); Dirk Fridag, Haltern am See (DE); Andrea Christiansen, Neu-Ulm (DE); Marc Becker, Dortmund (DE); Peter Wasserscheid, Erlangen (DE); Marco Haumann, Velden (DE); Michael Jakuttis, Sulzbach-Rosenberg (DE); Sebastian Werner, Berkeley, CA (US); Andreas Schoenweiz, Erlangen (DE)

(73) Assignee: Evonik Oxeno GmbH, Marl (DE)

( * ) Notice: Subject to any disclaimer, the term of this patent is extended or adjusted under 35 U.S.C. 154(b) by 159 days.

(21) Appl. No.: 13/822,650

(22) PCT Filed: Sep. 27, 2011

(86) PCT No.: PCT/EP2011/066760
§ 371 (c)(1),
(2), (4) Date: Jul. 9, 2013

(87) PCT Pub. No.: WO2012/041846
PCT Pub. Date: Apr. 5, 2012

(65) Prior Publication Data
US 2013/0289313 A1    Oct. 31, 2013

(30) Foreign Application Priority Data
Sep. 30, 2010   (DE) .................. 10 2010 041 821

(51) Int. Cl.
*B01J 31/22* (2006.01)
*C07C 45/50* (2006.01)
*B01J 31/02* (2006.01)
*B01J 31/18* (2006.01)

(52) U.S. Cl.
CPC .......... *B01J 31/2295* (2013.01); *B01J 31/0235* (2013.01); *B01J 31/0292* (2013.01); *B01J 31/185* (2013.01); *B01J 2231/321* (2013.01); *B01J 2531/822* (2013.01); *C07C 45/505* (2013.01)

(58) Field of Classification Search
CPC .......................... B01J 31/2295; C07C 45/505
USPC ..................... 568/455; 502/164, 166, 167
See application file for complete search history.

(56) References Cited

U.S. PATENT DOCUMENTS

| 7,193,116 B2 | 3/2007 | Moeller et al. |
| 7,317,130 B2 | 1/2008 | Moeller et al. |
| 7,495,134 B2 | 2/2009 | Hess et al. |
| 7,589,081 B2 | 9/2009 | Zapf et al. |
| 2011/0130595 A1 | 6/2011 | Lueken et al. |
| 2012/0123169 A1 | 5/2012 | Kaizik et al. |
| 2012/0190895 A1 | 7/2012 | Kaizik et al. |
| 2012/0197025 A1 | 8/2012 | Christiansen et al. |
| 2013/0030233 A1 | 1/2013 | Boeing et al. |

FOREIGN PATENT DOCUMENTS

| DE | 10 2008 002 187 | 12/2009 |
| WO | 2011 029691 | 3/2011 |
| WO | 2011 107441 | 9/2011 |
| WO | 2012 062558 | 5/2012 |

OTHER PUBLICATIONS

Riisager, A. et al., "Propene and 1-octene hydroformylation with silica-supported, ionic liquid-base (SILP) Rh-phosphine catalysts in continuous fixed-bed mode," Cayalysis Letters, vol. 90, Nos. 3-4, pp. 149 to 153, (Oct. 2003), XP-001194546.
Riisager, A. et al., "Catalytic SILP Materials," Top Organomet Chem, vol. 23, No. 23, pp. 149 to 161, (Jan. 1, 2008), XP-002663570.
International Search Report Issued Dec. 1, 2011 in PCT/EP11/66760 Filed Sep. 27, 2011.
U.S. Appl. No. 13/582,265, filed Mar. 11, 2013, Christiansen, et al.
U.S. Appl. No. 13/883,808, filed May 7, 2013, Franke, et al.
U.S. Appl. No. 13/703,925, filed Feb. 27, 2013, Franke, et al.
U.S. Appl. No. 13/988,431, filed May 20, 2013, Nordhoff, et al.

*Primary Examiner* — Porfirio Nazario Gonzalez
(74) *Attorney, Agent, or Firm* — Oblon, McClelland, Maier & Neustadt, L.L.P.

(57) ABSTRACT

The present invention provides a composition comprising: a) an inert porous support material, b) an ionic liquid, c) a metal selected from group 9 of the Periodic Table of the Elements, d) a phosphorus-containing organic ligand, e) at least one organic amine. The present invention further provides a process for hydroformylating olefin-containing hydrocarbon mixtures to aldehydes with addition of the inventive composition as a catalytically active composition, wherein: a) the water content of the olefin-containing hydrocarbon mixture is adjusted to not more than 20 ppm, b) the content of polyunsaturated compounds in the olefin-containing hydrocarbon mixture is adjusted to not more than 3000 ppm, c) a molar ratio of organic amines according to claims 10-13 to phosphorus-containing organic ligands according to claims 8-9 of at least 4:1 is established, d) a molar ratio of phosphorus-containing organic ligands according to claims 8-9 to rhodium of at least 10:1 is established.

19 Claims, 11 Drawing Sheets

USE OF SUPPORTED IONIC LIQUID PHASE (SILP) CATALYST SYSTEMS IN THE HYDROFORMYLATION OF OLEFIN-CONTAINING MIXTURES TO ALDEHYDE MIXTURES WITH A HIGH CONTENT OF ALDEHYDES UNBRANCHED IN THE 2 POSITION

Aldehydes with 5 to 11 carbon atoms which have a low content of isomer(s) branched in the 2 position are desired precursors for the production of a large number of products.

Thus for example $C_5$ aldehydes are starting materials for the production of pentanols, pentanoic acids and pentylamines. By aldol condensation and total hydrogenation of the aldol condensation product, decanols can be obtained from them, which are intermediates for the production of plasticizers, detergents and lubricants. Through their aldol condensation, hydrogenation of the olefinic double bond of the aldol condensation product and subsequent oxidation of the aldehyde group, decanoic acids can be obtained, which can for example be used for the production of lubricants or detergents. In this use field, it is important that the $C_5$ aldehydes to a large extent consist of the linear compound n-pentanal or that the content of branched $C_5$ aldehydes, such as in particular 2-methylbutanal, is as low as possible.

Likewise, $C_6$ aldehydes can be aldol condensed to dodecenals, which after total hydrogenation yield $C_{12}$ alcohols. These can for example be used for the production of detergents.

From $C_8$ to $C_{11}$ aldehydes, the corresponding alcohols, which are in particular used for the production of plasticizers, can be obtained by hydrogenation.

The production of aldehydes with a low content of isomers branched in the 2 position from olefins with internal double bonds requires that the olefins used be isomerized to 1-olefines, that the 1-olefines be terminally hydroformylated and that internal double bonds undergo hardly any hydroformylation.

The production of n-pentanal from 2-butene or mixtures thereof by isomerizing hydroformylation is described in DE 101 08 474, DE 101 08 475, DE 101 08 476 and DE102 25 282. The technical teaching of all these texts have in common that in at least one hydroformylation step a rhodium-containing catalyst system with a diphosphine ligand which contains a xanthene residue is used. With this catalyst system, 2-butenes can be hydroformylated under isomerizing conditions. The ratio of n-pentanal to 2-methylbutanal is at best about 85 to 15. The publications DE 101 08 474 and DE 101 08 475 describe processes wherein the hydroformylation takes place in two steps. In the first hydroformylation step, with the use of a catalyst system consisting of rhodium and a monophosphine as ligand, 1-butene is converted to n-pentanal with a selectivity of 90%. The unreacted butenes, mainly 2-butenes, are reacted in the second hydroformylation step with the use of the aforesaid catalyst system of rhodium/bisphosphine. The publications DE 101 08 476 and DE 102 25 282 describe single-step hydroformylation processes.

Higher selectivities for n-pentanal in the hydroformylation of 2-butenes can be obtained with the use of a catalyst system consisting of rhodium and sterically demanding aromatic bisphosphites, such as are for example described in EP 0 213 639. However, the selectivity decreases markedly with time.

Higher long-term selectivity and lower decomposition rates of the catalyst system are achieved when the catalyst system described in EP 0 213 639 is supplemented by a sterically hindered amine. A process with the use of this catalyst system for the hydroformylation of 2-butene to pentanal mixture with high n-pentanal mixture is disclosed in DE 10 2008 002187.3.

The hydroformylation of olefins with the use of rhodium-containing catalyst systems is essentially performed according to two basic modifications. In one, the Ruhrchemie/Rhone-Poulenc process, the catalyst system, consisting of rhodium and a water-soluble ligand, most often alkali metal salts of sulphonated phosphines, is dissolved in an aqueous phase. The educt-product mixture forms a second liquid phase. The two phases are mixed by stirring, and synthesis gas and olefin, if gaseous, are passed through them. The separation of the educt-product mixture from the catalyst system is effected by phase separation. The separated organic phase is worked up by distillation.

A disadvantage in this process, apart from the high capital outlay and the high operating costs, is the fact that only ligands stable to water can be used and that rhodium losses due to leaching are unavoidable.

In the other modification, the rhodium-containing catalyst system is homogeneously dissolved in an organic phase. Synthesis gas and starting olefin are passed into this phase. The reaction mixture withdrawn from the reactor is separated by distillation or membrane separation into a product-educt phase and a high-boiling phase, which contains the rhodium-containing catalyst system in solution. The phase containing the rhodium-containing catalyst system is returned to the reactor, and the other phase is worked up by distillation.

If appropriate, the aldehydes formed can be borne out of the reactor with excess synthesis gas, the catalyst system remaining in the reactor. However, this modification is only economic in the hydroformylation of olefins with at most 5 C atoms.

During the hydroformylation, high-boiling products are formed; for the most part these are aldol addition or aldol condensation products from the aldehydes formed. So that the high-boiling product concentration in the reactor remains limited, a side stream, as far as possible one in which the high-boiling products are concentrated, must be bled off. Rhodium compounds are contained in this side stream. In order to keep the rhodium losses small, rhodium must be recovered from this bleed stream. The separation of rhodium from such streams is costly and incomplete. Further rhodium losses occur due to cluster formation of the rhodium. These rhodium clusters deposit on the plant walls and in some cases form alloys with the plant materials. These quantities of rhodium are no longer catalytically active and even after shutdown of the plant can only be recovered partly and at great expense.

Since on account of the exceptionally high rhodium price in recent years the economic viability of an industrial hydroformylation process is largely dependent on the specific rhodium consumption, attempts were made to develop alternative processes which are characterized by lower specific rhodium losses.

In the development of new hydroformylation processes, the starting point was the idea of immobilizing the rhodium-containing catalyst systems, previously homogeneously present in the reaction mixtures. In this connection, this can be described as the heterogenization of a reaction itself performed homogeneously, in this case the hydroformylation. The most promising development until now is the hydroformylation of olefins to aldehydes by means of so-called Supported Ionic Liquid Phase (abbreviated as SILP) catalyst systems.

These are catalytically active compositions in a multiphase system, which consist of a solid, inert, porous, support material which is covered with an ionic liquid, the so-called SILP phase, which contains the catalyst containing the transition metal, in particular rhodium.

With SILP catalyst systems, the advantages of homogeneously and heterogeneously catalyzed synthesis reactions can be combined. This relates above all to the product separation and recovery of the catalyst, in particular of the transition metals contained therein, which is difficult and costly in homogeneously performed synthesis reactions. Conversely, in heterogeneously catalyzed synthesis reactions, mass and heat transfer limitation can occur, as a result of which the activity of the solid catalyst decreases; also, in heterogeneously catalyzed synthesis reactions lower chemo- and stereo-selectivities are observed.

Hydroformylation with the use of SILP catalyst systems has previously only been described in the literature for α-olefins, namely propene, 1-butene, 1-hexene and 1-octene:

A. Riisager, R. Fehrmann, P. Wasserscheid, R vanHal, Supported Ionic Liquid Phase Catalysis-Heterogenization of Homogeneous Rhodium Phosphine Catalysts, ACS Symposium Series 902 (2005), pp. 334-349

A. Riisager, R. Fehrmann, M. Haumann, P. Wasserscheid, SILP Catalysis in Gas Phase Hydroformylation and Carbonylation, DGMK Conference Report (2006), pp. 57-63

A. Riisager, R. Fehrmann, S. Flicker, R van Hal, M. Haumann, P. Wasserscheid, Very Stable and Highly Regioselective Supported Ionic-Liquid Phase (SILP) Catalysis: Continuous Flow Fixed-Bed Hydroformylation of Propene, Angewandte Chemie, International Edition, 2005, 44, 815-819

A. Riisager, R. Fehrmann, M. Haumann, P. Wasserscheid, Supported Ionic Liquid Phase (SILP) Catalysis: An Innovative Concept for Homogeneous Catalysis in Continuous Fix-Bed Reactors, Eur. J. Inorg. Chem. 2006, 695-706

Y. Yang, C. Deng, Y. Yuan, Characterization and hydroformylation performance of mesoporous MCM-41-supported water-soluble Rh complex dissolved in ionic liquids, Journal of Catalysis 232 (2005), 108-116

A. Riisager, R. Fehrmann, M. Haumann, B. S. K. Gorle, P. Wasserscheid, Stability and Kinetic Studies of Supported Ionic Liquid Phase Catalysts for Hydroformylation of Propene, Ind. Eng. Chem. Res. 2005, 44, 9853-9859

Riisager, S. Flicker, M. Haumann, P. Wasserscheid, R. Fehrmann, Supported Ionic Liquid Phase (SILP) Catalysts in Continuous Flow Processes, Proceedings-Electrochemical Society, 2006, 630-638

Riisager, K. M. Eriksen, P. Wasserscheid, R. Fehrmann, Propene and 1-Octene hydroformylation with silica-supported, ionic liquid phase (SILP) Rh-phosphine catalysts in continuous fixed-bed mode, Catalysis Letters, Vol. 90, Nos. 3-4, October 2003, 149-153)

Figure 1:
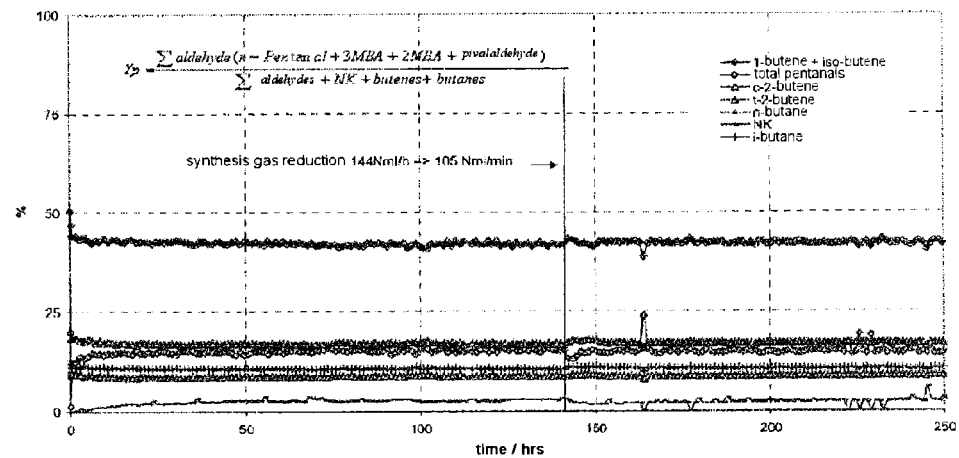
FIG. 1 shows hydroformylation of raffinate I with the use of the ligand of the formula VIII.

However, inter alia, insufficient catalyst shelf life has until now presented an obstacle to the implementation of the solution approach indicated in SILP catalysis on an industrial production scale. Likewise, for the industrial production scale it is necessary to start from a different raw material than the previously used pure α- or 1-olefins, e.g. the so-called raffinates, such as for example raffinate I, raffinate II, raffinate III and crude butane. These are by-products from petroleum refining and raffinate processing which are based on unsaturated hydrocarbon mixtures. These hydrocarbon mixtures contain only a proportion of the α- or 1-olefins necessary for the hydroformylation together with olefins with an internal double bond and multiply unsaturated compounds, such as for example 1,3-butadiene, saturated hydrocarbons and water.

For economic operation of a continuous process for the hydroformylation it is not only the use of a very active and selective catalyst that is important. A decisive part is in particular played by the aspects catalyst recycling, combined with product separation, and ligand stability—not only in view of the high rhodium and ligand prices, but also of the only approximately known influence of impurities from ligand degradation processes on the activity and the product spectrum.

It is generally known that organophosphorus ligands in hydroformylation are subject to an inherent degradation and deactivation process. [P. W. N. M. van Leeuwen, in Rhodium Catalyzed Hydroformylation, P. W. N. M. van Leeuwen, C. Clayer (Ed.), Kluwer, Dordrecht, 2000.]

Since some catalyst poisons such as water, alcohols, formic acid, oxygen or peroxides are always formed in traces or are technically unavoidable in a hydroformylation process, e.g. due to further reactions of the aldehydes, such as for example the aldol condensation, and further reactions of the synthesis gas, there is said to be an inherent, system-related instability of the catalyst system and the individual components thereof. Side reactions and degradation reactions can for example be hydrolysis, alcoholysis, transesterification, Arbusov rearrangement, P—O bond cleavage and P—C bond cleavage [P. W. N. M. van Leeuwen, in Rhodium Catalyzed Hydroformylation, P. W. N. M. van Leeuwen, C. Clayer (Ed.), Kluwer, Dordrecht, 2000.; F. Ramirez, S. B. Bhatia, C. P. Smith, Tetrahedron 1967, 23, 2067-2080.; E. Billig, A. G. Abatjoglou, D. R. Bryant, R. E. Murray, J. M. Maher, (Union Carbide Corporation), U.S. Pat. No. 4,789,753 1988; M. Takai, I. to Nakajima, T. Tsukahara, Y. Tanaka, H. Urata, A. Nakanishi, EP 1 008 581B1 2004.].

Ligand deactivation and degradation can take place not only during the actual reaction process, but also in the subsequent steps of product separation and catalyst recycling, e.g. due to thermal stress.

For the aforesaid reasons, in all large-scale industrial continuous hydroformylation processes operated in homogeneous phase, ligands and if necessary also the relevant transition metal are replenished, in order to be able to maintain the desired activity and selectivity over a long period.

It is economically desirable to be able to dispense with such catalyst replenishment.

Even with the use of catalytically active compositions based on SILP catalyst systems these are subject to comparable degradation mechanisms. The aforesaid inadequate catalyst lifetime in particular is an obstacle to implementation on the industrial scale, since, in contrast to the conventional hydroformylation processes, direct replenishment of ligands, and also of the relevant transition metal, is not possible.

Only through the presence of organic amines, abbreviated to OA, in the SILP phase is stabilization surprisingly achieved in such a manner that regular replenishment of the components of the catalytically active composition is not necessary for maintenance of the desired catalytic activity and selectivity, and the lifetime increases significantly. In this connection, the fact that through the use of a stripping gas the concentration of the aldehydes due to concentration in the SILP phase is markedly decreased has an additional favourable effect on the lifetime. As a result, interfering side reactions such as for example the aldol condensation, which lead to the deactivation and degradation of the catalytically active composition, are minimized.

On the basis of this, the problem comprised:
i) the provision of a suitable catalytically active composition for the hydroformylation of olefin-containing hydrocarbon mixtures under isomerizing conditions,
ii) the provision of a hydroformylation process with the use of this catalytically active composition for the production of aldehydes with a low content of isomers branched in the 2 position by hydroformylation of olefins with internal double bonds, which is characterized by a low specific rhodium consumption and low product losses due to further reactions of the target product and ensures a catalyst lifetime which enables transfer to the industrial scale and
iii) the provision of shaped bodies which are used in a fixed bed reactor, as well as slurry or fluidized bed process modifications.

Surprisingly it was found that olefins with 4 to 10 carbon atoms with an internal double bond can be hydroformylated with high selectivity to aldehydes unbranched in the 2 position if the hydroformylation is performed in the gas phase with a SILP catalyst system comprising rhodium, organophosphite ligands and at least one organic amine.

It was particularly surprising that these catalytically active compositions according to the invention exhibit higher lifetimes in the hydroformylation than the SILP catalyst systems described in the state of the art, which have phosphine derivatives as ligands. This finding is particularly surprising since in general phosphines are by orders of magnitude more stable to water, alcohols and aldehydes than phosphites.

Accordingly, the subject of the present invention is a composition comprising:
a) an inert, porous support material,
b) an ionic liquid,
c) a metal, selected from group 9 of the periodic table of the elements,
d) a phosphorus-containing organic ligand, and
e) at least one organic amine.

In a particular embodiment of the composition according to the invention the inert, porous support material is selected from the group comprising aluminium oxide, silicon dioxide, titanium dioxide, zirconium dioxide, silicon carbide, carbon and mixtures of these components.

In this particular embodiment, the inert, porous support material exhibits the following parameters:
a) BET surface area from 180 to 800 $m^2/g$
b) pore volume from 0.32 to 0.97 ml/g and
c) mean pore diameter from 2-50 nm.

In further embodiments of the composition according to the invention the inert, porous support material is selected from the group comprising:
mesoporous materials, microporous materials, macroporous materials, spongy materials, porous phosphates, porous polymers, polymer foams, metal foams, metallo-organic frameworks, porous nitrides, porous oxynitrides, and silicate-based aerogels. With regard to the porous phosphates as an inert, porous support material for the composition according to the invention, aluminium phosphates and structurally modified silicoaluminophosphates, such as for example SAPO-34, can be used.

As regards the porous nitrides or the porous oxynitrides as an inert, porous support material for the composition according to the invention, silicon nitride, boron nitride, carbon nitride or metallo-organic frameworks can be used.

With regard to the mesoporous materials as an inert, porous support material for the composition according to the invention, for example MCM-41-, MCM-48-, SBA-15-layer silicates or also flame-hydrolytically produced silicates can be used.

As regards the microporous materials as an inert, porous support material for the composition according to the invention, for example zeolites or alumosilicates can be used.

The inert, porous support materials for the composition according to the invention accessible in this way, after subsequent coating with
i) an ionic liquid,
ii) a metal of group 9 of the periodic table of the elements,
iii) a phosphorus-containing organic ligand, and
iv) at least one organic amine
are suitable for effecting the hydroformylation in a slurry modification of the process according to the invention, such as for example in the presence of a 2-phase gas-liquid reaction mixture, or as a fluidized bed modification of the process according to the invention, such as for example with a single-phase reaction mixture.

For the industrially interesting modification of performing the reaction in fixed bed reactors, it is firstly necessary that the previously described inert, porous support material be subjected to a shaping process, such as have long been known in the state of the art, with addition of a binder. As suitable binders, as well as aluminas, ceramic clays and colloids, for example alumosilicates, pyrogenic alumosilicates or amorphous zeolites can also be used. Advantageously, the inert porous support materials modified in this way are used in a form wherein they present a low flow resistance, such as for example in the form of shot, pellets or shaped bodies, such as for example tablets, cylinders, spheres, extrudates or rings.

Thus in general 1-20 weight %, based on the weight of the inert, porous support material, of a dry binder as aforesaid together with temporary additives, such as for example water, aqueous solutions, water substitutes, such as for example glycols, polyglycols and also fixatives, such as for example cellulose ethers, are vigorously mixed. This process can for example be performed in a kneader. Next, the shaped bodies for the solid bed reactor are produced by a shaping process, such as for example pelleting, extrusion or dry pressing. Before installation, the shaped bodies are calcined in a temperature range from 200-700° C., whereby the temporary additives are removed.

In this respect, a further embodiment of the composition according to the invention is characterized in that from the inert, porous support material, such as for example silicon dioxide, with the use of an additional binder, selected from the group comprising:
a) alumina,
b) ceramic clays, and
c) colloids
shaped bodies of different three-dimensional form, selected from the group containing:
i) spherical,
ii) cylindrical,
iii) ellipsoidal and
iv) polylobular bodies
are formed in a size range from 1-10 mm.

A further, particular embodiment of the composition according to the invention is characterized in that as the ionic liquid compounds are used wherein the anion is selected from the group comprising:
Tetrafluoroborate ([BF$_4$]$^-$), hexafluorophosphate ([PF6]$^-$), dicyanamide ([N(CN)$_2$]$^-$), bis(trifluoromethylsulphonyl) imide ([NTf$_2$]$^-$), tricyanomethide ([C(CN)$_3$]$^-$), tetracyanoborate ([B(CN)$_4$]$^-$), halide (Cl$^-$, Br$^-$, F$^-$, I$^-$), hexafluoroantimonate ([SbF$_6$]$^-$), hexafluoroarsenate ([AsF$_6$]$^-$), sulphate ([SO$_4$]$^{2-}$), tosylate ([C$_7$H$_7$SO$_3$]$^-$), triflate ([CF$_3$SO$_3$]$^-$), nonaflate ([C$_4$F$_9$SO$_3$]$^-$), tris-(pentafluoroethyl)-trifluorophosphate ([PF$_3$(C$_2$F$_6$)$_3$]$^-$), thiocyanate ([SCN]$^-$), carbonate ([CO$_3$]$^{2-}$), [R'—COO]$^-$, [R'—SO$_3$]$^-$, [R'—PO$_4$R"]$^-$ or [(R'—SO$_2$)$_2$N]$^-$ with R' and R" the same or different, and each is a linear or branched aliphatic or alicyclic residue containing 1 to 12 carbon atoms or a C5-C18 substituted aryl, C5-C18 substituted aryl-C1-C6 alkyl or C1-C6 alkyl-05-C18 substituted aryl residue, which can be substituted with halogen atoms;
wherein the cation is selected from the group comprising:
quaternary ammonium cations of the general formula [NR1R2R3R4]+; phosphonium cations of the general formula [PR1R2R3R4]+; imidazolium cations of the general formula

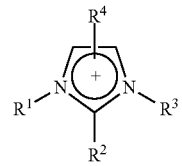

wherein the imidazole nucleus can be substituted with at least one group R, which is selected from C1-C6 alkyl, C1-C6 alkoxy, C1-C6 substituted aminoalkyl, C5-C12 substituted aryl or C5-C12 substituted aryl-C1-C6 alkyl groups; pyridinium cations of the general formula

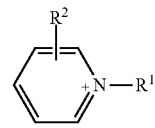

wherein the pyridine nucleus can be substituted with at least one group R, which is selected from C1-C6 alkyl, C1-C6 alkoxy, C1-C6 substituted aminoalkyl, C5-C12 substituted aryl or C5-C12 substituted aryl-C1-C6 alkyl groups; pyrazolium cations of the general formula

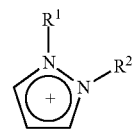

wherein the pyrazole nucleus can be substituted with at least one group R, which is selected from C1-C6 alkyl, C1-C6 alkoxy, C1-C6 substituted aminoalkyl, C5-C12 substituted aryl or C5-C12 substituted aryl-C1-C6 alkyl groups; and triazolium cations of the general formula

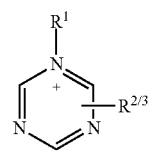

wherein the triazole nucleus can be substituted with at least one group R, which is selected from C1-C6 alkyl, C1-C6 alkoxy, C1-C6 substituted aminoalkyl, C5-C12 substituted aryl or C5-C12 substituted aryl-C1-C6 alkyl groups, and the residues R1, R2, R3 independently of one another are selected from the group consisting of:
hydrogen;
linear or branched, saturated or unsaturated, aliphatic or alicyclic alkyl groups with 1 to 20 carbon atoms;
heteroaryl and heteroaryl-C1-C6 alkyl groups with 3 to 8 carbon atoms in the heteroaryl residue and at least one hetero atom selected from N, O and S, which can be substituted with at least one group selected from C1-C6 alkyl groups and/or halogen atoms; and
aryl and aryl-C1-C6 alkyl groups with 5 to 12 carbon atoms in the aryl residue, which can optionally be substituted with at least one C1-C6 alkyl group and/or one halogen atom.

A particularly preferred further embodiment of the composition according to the invention is characterized in that the ionic liquid is selected from the group comprising:
a) 1-ethyl-3-methylimidazolium bis(trifluoromethylsulphonyl)imide,
b) 1-butyl-3-methylimidazolium hexafluorophosphate, and
c) 1-butyl-3-methylimidazolium tetrafluoroborate.

A further, particular embodiment of the composition according to the invention is characterized in that the metal selected from group 9 of the periodic table of the elements is rhodium.

A particular embodiment of the composition according to the invention is characterized in that the phosphorus-containing organic ligand contains at least one covalent bond, which is selected from the group consisting of:
a) phosphorus-oxygen; and
b) phosphorus-nitrogen.

A particularly preferred embodiment of the composition according to the invention is characterized in that the phosphorus-containing organic ligand is selected from the group comprising:
a) [6,6'-((3,3'-di-tert-butyl-5,5'-dimethoxy-[1,1'-biphenyl]-2,2'-diyl)bis(oxy))bis(dibenzo[d,f][1,3,2]dioxaphosphepine)] according to formula VII

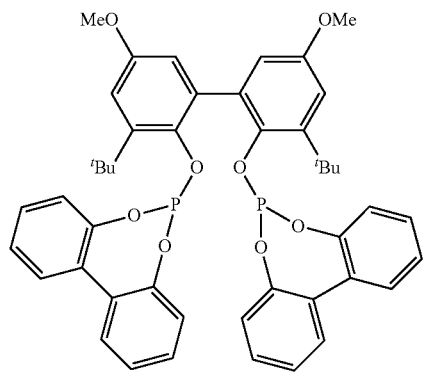

b) [2,2'-((3,3'-di-tert-butyl-5,5'-dimethoxy-[1,1'-biphenyl]-2,2'-diyl)bis(oxy))bis(4,4,5,5-tetraphenyl-1,3,2-dioxaphospholane)] according to formula VIII and

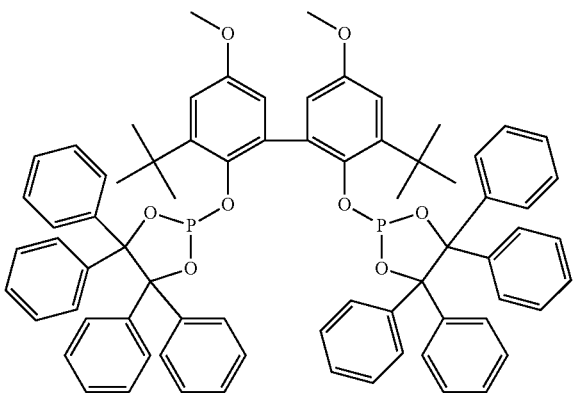

c) tris-(2,4-di-tert-butylphenyl)phosphite according to formula IX

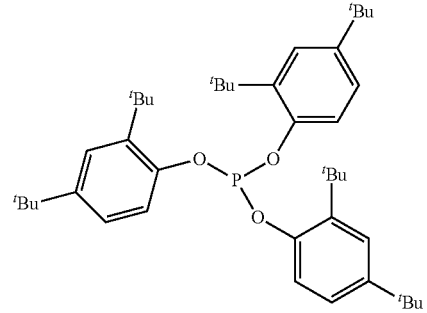

In a particular embodiment of the composition according to the invention the organic amine OA is selected from the group comprising:
a) at least one amine according to formula X

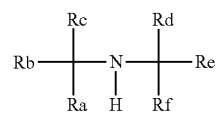

wherein Ra, Rb, Rc, Rd, Re and Rf are the same or different hydrocarbon residues, which can also be bound to one another, and
b) a tertiary amine, selected from the group of the aliphatic, aromatic, cycloaliphatic and heteroaromatic amines, or combinations thereof.

A further, particular embodiment of the composition according to the invention is characterized in that the organic amine OA contains at least one compound with a 2,2,6,6-tetramethylpiperidine unit according to the formula XI:

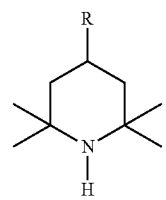

wherein R represents an organic residue, hydrogen, a hydroxyl group or a halogen.

The organic residue R in the structure of the formula XI can also be an organic residue bound to the 2,2,6,6-tetramethylpiperidine structural unit via a hetero atom, for example an oxygen atom. In particular, the organic residue can contain polymeric structures or be an organic residue containing 1 to 50 carbon atoms and optionally hetero atoms. Particularly preferably, the organic residue contains carbonyl groups, such as keto, ester or acid amide groups. The organic residue optionally containing hetero atoms can in particular be a substituted or unsubstituted, aliphatic, alicyclic, aliphatic-alicyclic, heterocyclic, aliphatic-heterocyclic, aromatic, aromatic-aromatic or aliphatic-aromatic hydrocarbon residue with 1 to 50 carbon atoms, wherein the substituted hydrocarbon residues can have substituents selected from primary, secondary or tertiary alkyl groups, alicyclic groups, aromatic groups, —N(R1)2, —NHR1, —NH2, fluorine, chlorine, bromine, iodine, —CN, —C(O)—R1, —C(O)H or —C(O)O—R1, —CF3, —O—R1, —C(O)N—R1, —OC(O)R1 and/or —Si(R1)3, with R1 equal to a monovalent hydrocarbon residue, preferably having 1 to 20 carbon atoms. If several hydrocarbon residues R1 are present, then these can be the same or different. The substituents are preferably limited to those which have no influence on the reaction itself. Particularly preferable substituents can be selected from the halogens, such as for example chlorine, bromine or iodine, the alkyl residues, such as for example methyl, ethyl, propyl, iso-propyl, butyl, sec-butyl, t-butyl, neo-pentyl, sec-amyl, t-amyl, iso-octyl, t-octyl, 2-ethylhexyl, iso-nonyl, iso-decyl or octadecyl, the aryl residues, such as for example phenyl, naphthyl or anthracyl, the alkylaryl residues, such as for example tolyl, xylyl, dimethylphenyl, diethylphenyl, trimethylphenyl, triethylphenyl or p-alkylphenyl, the aralkyl residues, such as for example benzyl or phenylethyl, the alicyclic residues, such as for example cyclopentyl, cyclohexyl, cyclooctyl, cyclohexylethyl or 1-methylcyclohexyl, the alkoxy residues, such as for example methoxy, ethoxy, propoxy, butoxy or pentoxy, the aryloxy residues, such as for example phenoxy or naphthoxy, —OC(O)R1 or —C(O)R1, such as for example acetyl, propionyl, trimethylacetoxy, triethylacetoxy or triphenylacetoxy, and the silyl residues —Si(R1)3 have three carbon residues, such as for example trimethyl-silyl, triethylsilyl or triphenylsilyl. Particularly preferable are compounds of the formula XIa which as the residue R have those which contain a 2,2,6,6-tetramethylpiperidine residue and optionally a further —N(R1)2, —NHR1 and/or —NH2 group or mixtures thereof.

A particularly preferred embodiment of the composition according to the invention is characterized in that the organic amine OA has at least one of the compounds according to the formulae XIa to XIh:

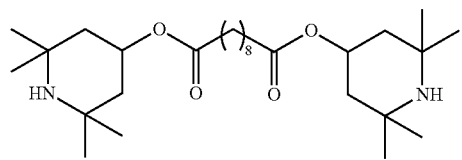

XIa

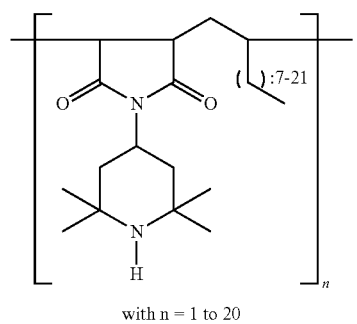

XIb with n = 1 to 20

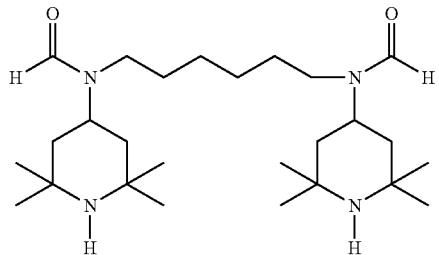

XIc

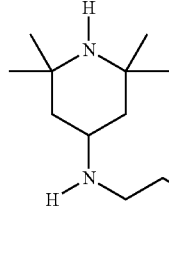

XId

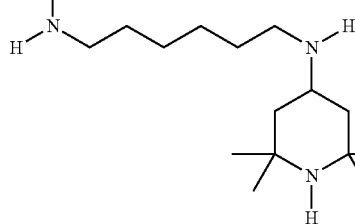

XIe with n = 1 to 12

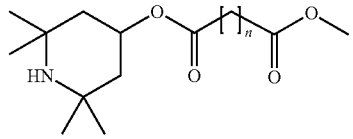

XIf with n = 1 to 17

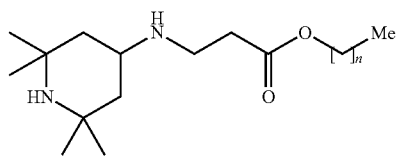

XIg

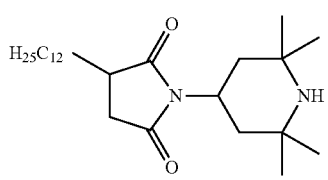

XIh with R = C6 to C20 alkyl

A quite particularly preferable embodiment of the composition according to the invention is characterized in that a further organic amine according to the formulae XIIa to XIIj:

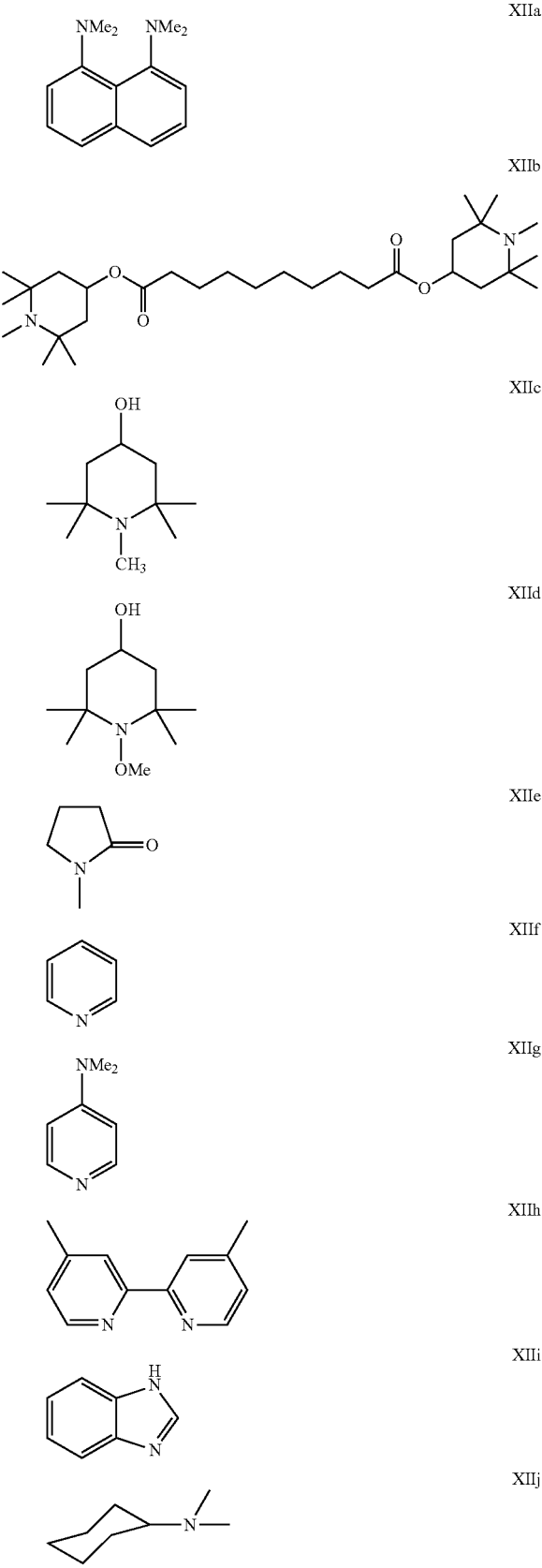

is present.

A particular embodiment of the present invention is a multiphase reaction mixture, containing:
a) an olefin-containing hydrocarbon mixture,
b) a gas mixture comprising carbon monoxide and hydrogen and
c) aldehydes,
characterized by the composition according to the invention as the catalytically active composition.

A further subject of the present invention is a process for the hydroformylation of olefin-containing hydrocarbon mixtures to aldehydes with addition of the composition according to the invention as the catalytically active composition, wherein:
a) the water content of the olefin-containing hydrocarbon mixture is adjusted to at most 20 ppm,
b) the content of multiply unsaturated compounds in the olefin-containing hydrocarbon mixture is adjusted to at most 3000 ppm,
c) a molar ratio of organic amines, selected from the group comprising the formulae X, XI, XIa-XIh, XIIa-XIIj, to phosphorus-containing organic ligands according to the formulae VII, VIII or IX, of at least 4:1 is set, and
d) a molar ratio of phosphorus-containing organic ligands according to the formulae VII, VIII or IX to rhodium of at least 10:1 is set.

As regards the reaction temperature of the process according to the invention, in a particular embodiment this is performed in a range from 60-150° C., in particular from 70-140° C., particularly preferably from 80-120° C.

With regard to the reaction pressure of the process according to the invention, in a particular embodiment this is performed in a range from 0.01-6.0 MPa absolute, in particular from 0.5-5.0 MPa absolute, particularly preferably from 1.0-2.5 MPa absolute. A particular embodiment of the process according to the invention is characterized in that the reaction mixture is periodically subjected to a stripping gas treatment to strip out the aldehydes.

A particularly preferred embodiment of the process according to the invention is characterized in that the stripping gas is selected from the group comprising:
a) mixtures of carbon monoxide and hydrogen;
b) mixtures of C2-C6 alkanes;
c) mixtures of C2-C6 alkanes and C2-C6 alkenes; and
d) inert gases.

A further, particularly preferable embodiment of the process according to the invention is characterized in that after conclusion of the reaction a part of the gaseous reaction mixture is fed back into the reaction zone again.

A particular embodiment of the process according to the invention is characterized in that the separation of the product from the reaction zone is effected by a process step selected from the group comprising:
a) extraction,
b) condensation,
c) absorption
d) adsorption and
e) pervaporation.

A further, particularly preferable embodiment of the process according to the invention is characterized in that the olefin-containing hydrocarbon mixture is selected from the group comprising:
a) ethylene,
b) propylene,
c) C4-olefins and multiply unsaturated compounds, and
d) C5-olefins and multiply unsaturated compounds.

A further subject of the present invention is a process for the production of aldehydes with 5 to 11 carbon atoms with a low proportion of isomers branched in the 2 position by hydroformylation of olefins with 4 to 10 carbon atoms with an internal double bond, with addition of the composition according to the invention as the catalytically active composition.

A process for the production of n-pentanal from 2-butene-containing mixtures is in particular a subject of the invention.

The present invention has the following advantages compared to conventional processes:

Almost all of the rhodium used remains in the catalytically active composition during the hydroformylation. With the removal of the deactivated SILP catalyst system, almost the whole quantity of rhodium used is removed from the plant. For the recovery of the rhodium, only the relatively small quantity of the catalytically active composition needs to be processed. This lowers the costs for the processing and decreases the rhodium losses. This results in low specific rhodium costs for the hydroformylation process. The selectivity of the formation of the aldehydes is high. The degradation of the ligands is slow, resulting in low ligand costs and a long lifetime for the catalytically active composition.

Processes for the hydroformylation of olefin-containing hydrocarbon mixtures to aldehydes with the use of the catalytically active composition according to the invention are described in more detail below.

EXAMPLES

All the operations performed are performed with maintenance of the blanket gas atmosphere (argon).

Example 1

Preparation of the SILP Catalyst System

As the inert, porous support material, silicon dioxide is heated at 450° C. over 24 hrs for calcination or thermal pretreatment, which is followed by a further 24 hrs under vacuum at 200 Pa. Thereafter, the silicon dioxide is stored under an argon atmosphere. 0.052 g of 0.2 mmol of rhodium dicarbonylacetylacetonate (abbreviation Rh(acac)(CO)$_2$) is dissolved in ca. 50 ml of CH$_2$Cl$_2$ and stirred for 10 mins. Next, 2 mmol of the particular phosphorus-containing organic ligand L of the formula VII, VIII or IX used is added with stirring. After a further 10 minutes, 8 mmol of the organic amine bis(2,2,6,6-tetramethyl-4-piperidyl)sebacate (abbreviation OA) are added. The addition of the ionic liquid IL, e.g. 1-ethyl-3-methylimidazolium bis(trifluoromethanesulphonyl)imide, abbreviation [EMIM][NTf$_2$], is effected after a further 10 mins stirring, whereby a loading level a is set such that it assumes a value from 0.1 or 10 vol. % respectively. In connection with SILP catalyst systems, a loading level a is understood to mean the ratio of the volume of the particular ionic liquid IL used to the pore volume of the particular support material used. The aforesaid value of the loading level a of 0.1 or 10 vol. % respectively was determined from preliminary experiments. It represents an optimum as regards the catalytic activity-typically stated as TOF or turnover frequency in hr$^{-1}$- and the retention of the particular transition metal-containing complex compounds used on the inert, porous support material. After a further 30 mins, 10 g of calcined silicon dioxide (Silica 100, Merck) are added and a rhodium loading of the SILP catalyst systems $m_{Rh}$ of 0.2 weight % is thus set. After ca. 60 mins, the solvent is cautiously removed on the rotary evaporator and the product is then stored under argon until use.

Before the start of an experiment, the SILP catalyst system is preformed each time for 24 hrs at 100° C., 1.0 MPa and with a synthesis gas (a mixture of CO and H$_2$ in the ratio 1:1) flow rate of 100 Nml/min.

Example 2

Experimental Procedure

A continuous gas phase apparatus consisting of metering unit, evaporator unit, mixer, reaction section and condensation section is used for the hydroformylation reaction.

The substrate to be hydroformylated is passed into the evaporator (T=160° C.) via an HPLC pump and brought to reaction temperature with the synthesis gas stream. After passage through the catalyst bed, a side-stream is sent for gas analysis and the remaining stream condensed out (for further analytical purposes).

Example 3

Hydroformylation of Raffinate I with the Use of the Ligand of the Formula VIII 12 g of the catalyst prepared according to example 1 are installed in the apparatus while maintaining the blanket gas atmosphere, and preformed as described. Next, the reaction is started by connection of the raffinate stream.

Parameters: 1.0 MPa, 144 Nml/min (CO/H$_2$), reduction to 105 Nml/min beyond 141 hrs, 0.15 ml of raffinate I (liquid), T(evaporator): 160° C., T(reactor):100° C. A raffinate I is used which contains at most 3000 ppm of multiply unsaturated hydrocarbon compounds, such as for example 1,3-butadiene. In addition, a water content of at most 20 ppm is ensured by standard techniques, such as for example molecular sieve. The residence time of the reaction gas on the catalyst bed is ca. 12.5 secs. After attainment of a steady state, the following product mixture is obtained over a period of 250 hrs:

| | Composition of raffinate I (anhydrous)/%[1] | Composition of product gas/%[2] |
|---|---|---|
| 1-butene + isobutene | 60 (17 + 43) | 41 |
| Σ pentanals | | 15 |
| cis-butene | 8 | 10 |
| trans-butene | 17 | 16 |
| n-butane | 11 | 10 |
| i-butane | 4 | 5 |
| side components SC | | 3 |

[1]GC % areas (column silica 50 m * 0.32 mm, coating Al2O3/Na2SO4, DF = 5 μm; carrier gas helium, 91.6 ml/min; carrier gas pressure 0.12 MPa; detector: FID; evaporator temperature: 200° C., temperature program: 120° C. isothermal, 10 mins)
[2]Weight percent calculated from GC percentage area (HP Pona 50 m * 200 μm * 0.5 μm; carrier gas helium 74 ml/min, carrier gas pressure 0.36 MPa; detector: FID; evaporator temperature: 200° C.; temperature program: 50° C.-200° C., 15 mins isothermal, 25° C./min up to 200° C., 40 mins isothermal The selectivity S for n-pentanal within the aldehydes formed is >99% and is calculated according to the following formula:

$S_n$=n-pentanal/Σaldehyde

Σaldehyde=n-pentanal+3-MBA+2-MBA+pivalaldehyde

Illustration 1 Corresponds to FIG. 1

Example 4

Hydroformylation of Crude Butane with Use of the Ligand of the Formula VII 12 g of the SILP catalyst system prepared according to Example 1 with the following composition (0.052 g Rh(acac)

(CO)$_2$, 1.57 g VII, 3.85 g OA, 1.5 g [EMIM][NTf$_2$], 10 g Silica 100) are installed in the apparatus while maintaining the blanket gas atmosphere and preformed as described. Next the reaction is started by connection of the crude butane stream. On the basis of its origin as a process side-stream, the C4-containing olefin mixture crude butane is to be regarded as free from multiply unsaturated to hydrocarbon compounds, such as for example 1,3-butadiene, down to a detection limit of 1 ppm. Residual contents of water are reduced to at most 20 ppm, as already described in Example 3.

Parameters: 1.0 MPa, 144 Nml/min (CO/H$_2$), 0.15 ml/min crude butane (liquid), T(evaporator): 160° C., T(reactor): 100° C., or 120° C. respectively.

Figure 2:
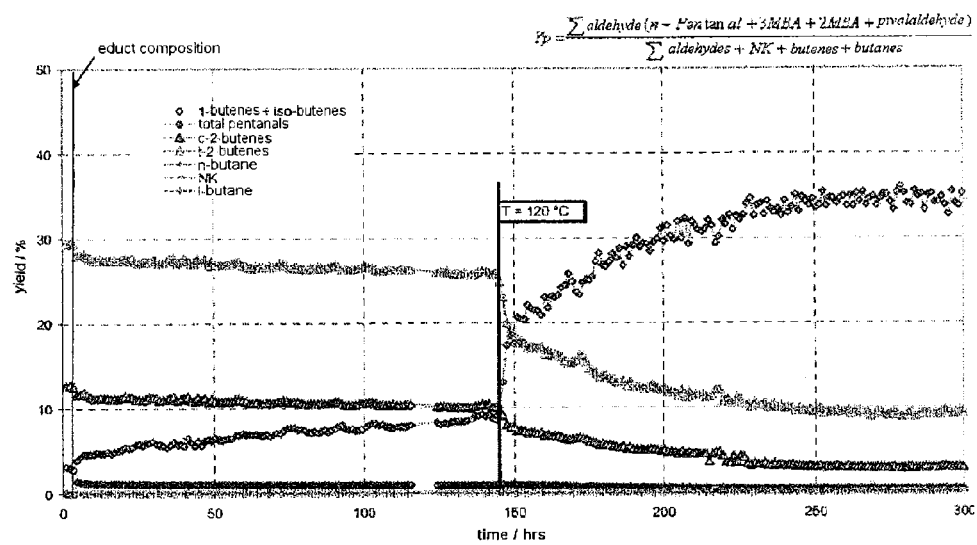
FIG. 2 shows hydroformylation of crude butane with use of the ligand of the formula VII.

Illustration 2 Corresponds to FIG. 2

TABLE

| | Composition of crude butane/%[1] | Composition of product stream 100° C./%[2] | Composition of product stream 120° C./%[2] |
|---|---|---|---|
| 1-butene/isobutene | 3 (2 + 1) | 1 | 41 |
| Σ pentanals | | 7 | 15 |
| cis-butene | 11 | 10 | 10 |
| trans-butene | 29 | 26 | 16 |
| n-butane | 57 | 54 | 10 |
| i-butane | <1 | <1 | 5 |
| side components SC | | <1 | 3 |
| n-selectivity | | 97 | 95 |

[1]GC % areas (column silica 50 m * 0.32 mm, coating Al2O3/Na2SO4, DF = 5 µm; carrier gas helium, 91.6 ml/min; carrier gas pressure 0.12 MPa; detector: FID; evaporator temperature: 200° C., temperature program: 120° C. isothermal, 10 mins)
[2]Weight percent calculated from GC percentage area (HP Pona 50 m * 200 µm * 0.5 µm; carrier gas helium 74 ml/min, carrier gas pressure 0.36 MPa; detector: FID; evaporator temperature: 200° C.; temperature program: 50° C.-200° C., 15 mins isothermal, 25° C./min up to 200° C., 40 mins isothermal The selectivity for n-pentanal is stated within the aldehydes formed.

Example 5

Hydroformylation of a C4 olefin mixture with use of the ligand of formula VII 12 g of the catalyst prepared according to Example 1 with the following composition (0.103 g Rh(acac)(CO)$_2$, 3.15 g VII, 7.69 g OA, 3 g [EMIM][NTf$_2$], 20 g Silica 100) are installed in the apparatus while maintaining the blanket gas atmosphere and preformed as described. Next the reaction is started by connection of the C4 olefin mixture.

Parameters: 1.0 MPar 144 Nml/min (CO/H2), 0.15 ml/min C4 olefin mixture (liquid), T(evaporator): 160° C., T(reactor): 120° C.

After attainment of a steady state, the following product mixture is obtained:

| | Composition of C4 mixture/%[1] | Composition of product gas/%[2] |
|---|---|---|
| 1-butene/isobutene | 60 (18 + 42) | 21 |
| Σ pentanals | | 52 |
| cis-butene | 8 | 2 |
| trans-butene | 15 | 8 |
| n-butane | 13 | 11 |
| i-butane | 4 | 4 |
| side components SC | | 2 |
| n-selectivity | | 60 |

Figure 3:
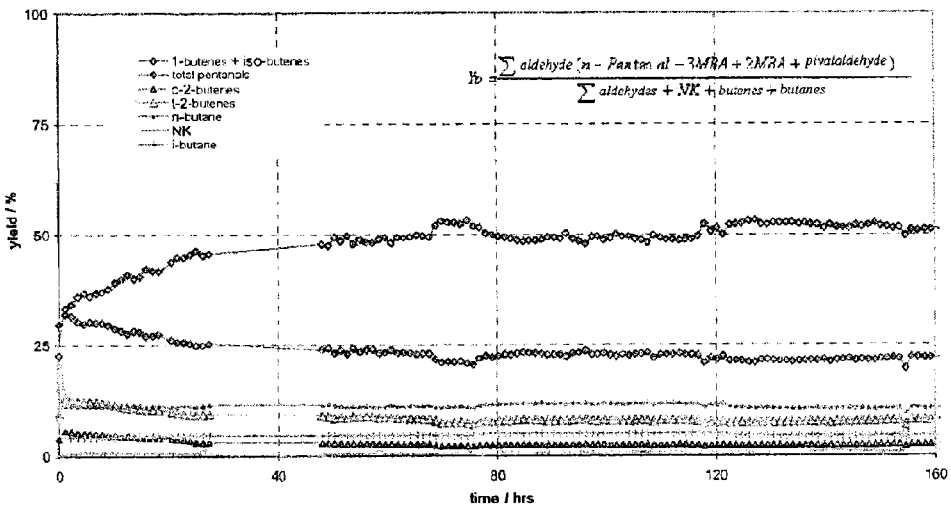
FIG. 3 shows hydroformylation of a C4 olefin mixture with use of the ligand of formula VII.

[1]GC % areas (column silica 50 m * 0.32 mm, coating Al2O3/Na2SO4, DF = 5 µm; carrier gas helium, 91.6 ml/min; carrier gas pressure 0.12 MPa; detector: FID; evaporator temperature: 200° C., temperature program: 120° C. isothermal, 10 mins)
[2]Weight percent calculated from GC percentage area (HP Pona 50 m * 200 µm * 0.5 µm; carrier gas helium 74 ml/min, carrier gas pressure 0.36 MPa; detector: FID; evaporator temperature: 200° C.; temperature program: 50° C.-200° C., 15 mins isothermal, 25° C./min up to 200° C., 40 mins isothermal Illustration 3 Corresponds to FIG. 3

The selectivity for n-pentanal is stated within the aldehydes formed.

Example 6

Hydroformylation of Raffinate III with Use of the Ligand of Formula VII 12 g of the catalyst prepared according to Example 1 with the following composition (0.103 g Rh(acac)(CO)$_2$, 3.15 g VII, 7.69 g OA, 3 g [EMIM][NTf$_2$], 20 g Silica 100) are installed in the apparatus while maintaining the blanket gas atmosphere and preformed as described. Next the reaction is started by connection of the raffinate stream. On the basis of its origin as a process side-stream, the C4-containing olefin mixture raffinate III is to be regarded as free from multiply unsaturated hydrocarbon compounds, such as for example 1,3-butadiene, down to a detection limit of 1 ppm. Residual contents of water are reduced to at most 20 ppm, as already described in Example 3.

Parameters: 1.0 MPa, 144 Nml/min (CO/H$_2$), 0.15 ml/min raffinate III (liquid), T(evaporator): 160° C., T(reactor): 120° C.

After attainment of a steady state, the following product mixture is obtained:

| | Composition of raffinate III/%[1] | Composition of product stream/%[2] |
|---|---|---|
| 1-butene/isobutene | (30 + <1) | 1 |
| Σ pentanals | | 51 |
| cis-butene | 16 | 8 |
| trans-butene | 32 | 21 |
| n-butane | 21 | 17 |
| i-butane | <1 | <1 |
| side components SC | | 1 |
| n-selectivity | | 96 |

Figure 4:
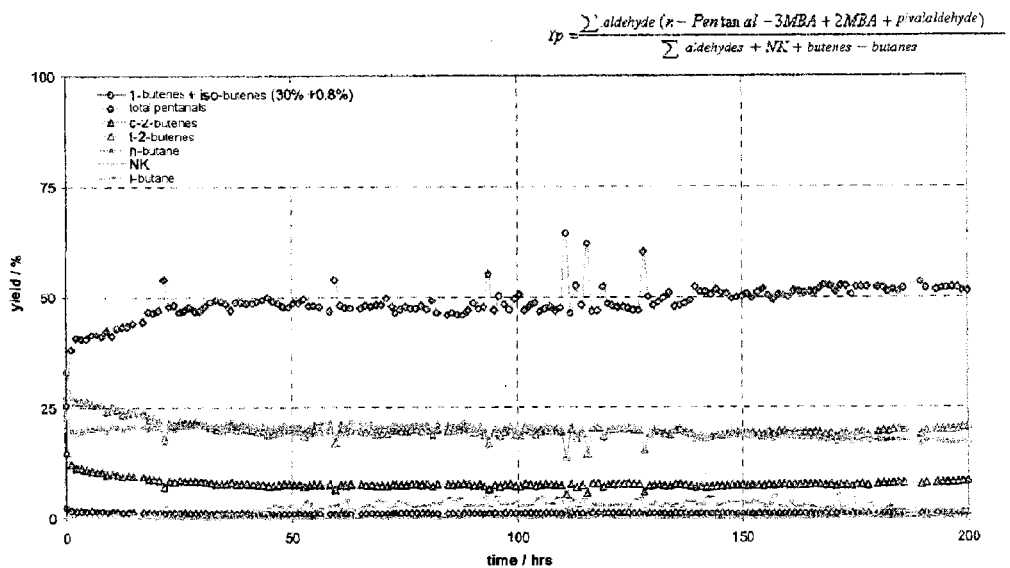
FIG. 4 shows hydroformylation of raffinate III with use of the ligand of formula VII.

[1]GC % areas (column silica 50 m * 0.32 mm, coating Al2O3/Na2SO4, DF = 5 µm; carrier gas helium, 91.6 ml/min; carrier gas pressure 0.12 MPa; detector: FID; evaporator temperature: 200° C., temperature program: 120° C. isothermal, 10 mins)
[2]Weight percent calculated from GC percentage area (HP Pona 50 m * 200 µm * 0.5 µm; carrier gas helium 74 ml/min, carrier gas pressure 0.36 MPa; detector: FID; evaporator temperature: 200° C.; temperature program: 50° C.-200° C., 15 mins isothermal, 25° C./min up to 200° C., 40 mins isothermal Illustration 4 Corresponds to FIG. 4

Example 7

Experimental Series for the Hydroformylation of Isobutene

In a reaction in the plug-flow reactor, a phosphite ligand was for the first time used in an SILP catalyst system. The purpose of the experiments was to achieve the highest possible activity and stability for the SILP catalyst system. A selectivity problem is not to be expected with isobutene, since because of the steric and electronic conditions almost exclusively the terminal 3-methylbutyraldehyde (abbreviation 3-MBA) is formed.

Scheme 1. Simplified mechanism for isobutene hydroformylation

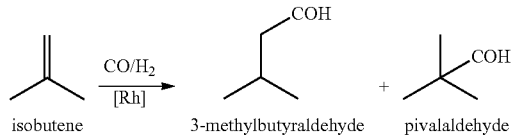

Hence the sterically demanding phosphite ligand L according to formula IX, 2,4-di-t-Bu triphenylphosphite, which is known for high activity towards slow-reacting alkenes, is used.

From preliminary experiments, it was known that phosphites are decomposed in the hydroformylation in the presence of water. Hence in the experiments described here three strategies were tried for suppressing this decomposition in order to obtain long-term storage-stable SILP catalyst systems. Firstly, the effect of the ligand excess on the stability was investigated. Further, organic amines (abbreviation OA) were added in order to prevent ligand degradation. As a third modification, traces of water were to be removed from the substrate through a so-called guard bed above the catalyst bed and the lifetime of the catalyst thus increased.

In all experiments, SILP catalyst systems were prepared which contained Silica 100 (63-200 μm) from Merck as the support material, which was calcined at 450° C. for 24 hrs.

In the first experiment, a molar ligand/rhodium ratio L/Rh of 10 was used. From 0 it appears that at 100° C. and 1.0 MPa the conversion very rapidly rose to a steady-state value of ca. 21%. After a few hours, there was a slight, linear decline in the conversion. No significant increase in conversion could be achieved by a temperature increase to 110° C. At 120° C. the conversion rose slightly and for more than 30 hours could be maintained at a conversion level of 20%. Thereafter with the same setting the activity of the SILP catalyst system began to fall markedly. A temperature and pressure increase gave no change in this (see. Table 1, Experiment 4-5).

TABLE 1

Hydroformylation of isobutene with Rh-2,4-di-t-Bu triphenylphosphite SILP catalyst system

| Expt. | T/° C. | p/MPa | τ/sec | X/% | TOF/ $hr^{-1}$ | n/iso sel./% | STY/ $kgl_{cat}^{-1}hr^{-1}$ | GHSV/ $ll_{cat}^{-1}hr^{-1}$ | Stability/ hr |
|---|---|---|---|---|---|---|---|---|---|
| 1 | 100 | 1.0 | 28 | 20.7 | 287.2 | 99.8 | 0.09 | 4.98 | 19 |
| 2 | 110 | 1.0 | 28 | 21.2 | 293.5 | 99.9 | 0.09 | 5.23 | 6 |
| 3 | 120 | 1.0 | 28 | 20.3 | 281.4 | 99.8 | 0.09 | 5.14 | 33[1] |
| 4 | 130 | 1.0 | 28 | 4.5 | 63.0 | 99.7 | 0.02 | 1.18 | — |
| 5 | 130 | 2.0 | 26 | 10.3 | 143.0 | 99.8 | 0.04 | 1.34 | — |

[1]Deactivation takes place after a total experiment run time of 58 hrs. The activity and selectivity of Experiments 4 and 5 relate to the initial activity, since the SILP catalyst system already deactivates.
Experimental conditions: T = 100-130° C., p = 1.0-2.0 MPa, τ = 26-28 secs, $H_2:CO = 1$, Volume flow$_{isobutene}$ = 1.8-3.5 ml min$^{-1}$, Volume flow$_{H2}$ = Volume flow$_{CO}$ = 6.8-8.3 ml min$^{-1}$, $m_{SILP}$ = 3.0 g, $m_{Rh}$ = 0.2%, L/Rh = 10, $α_{IL}$ = 10 vol. % (IL = [EMIM][NTf$_2$]).

Figure 5:
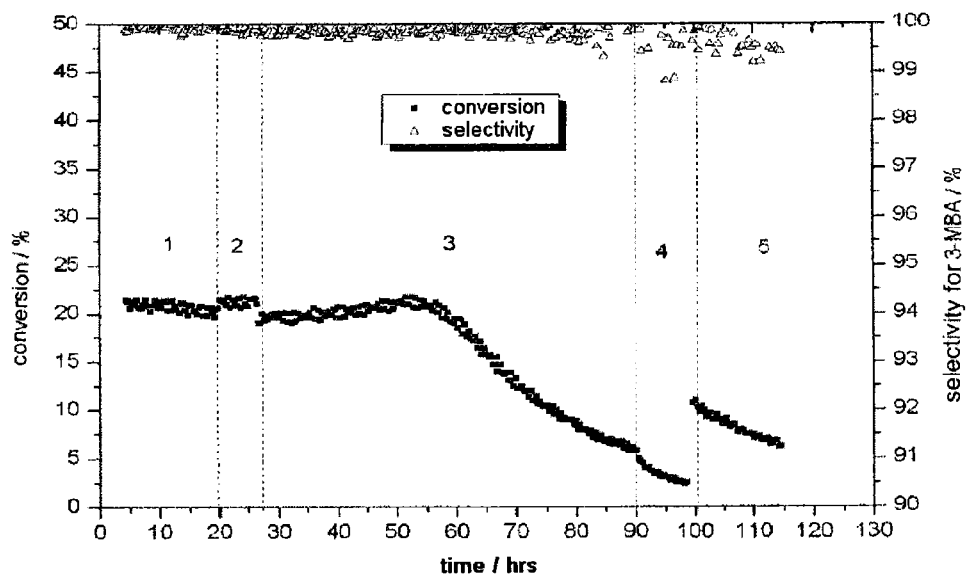
FIG. 5 shows hydroformylation of isobutene with Rh-2,4-di-t-Bu triphenylphosphite SILP catalyst system (ligand/rhodium =10).

Illustration 5 Corresponds to FIG. 5

Illustration 5. Hydroformylation of isobutene with Rh-2,4-di-t-Bu triphenylphosphite SILP catalyst system (ligand/rhodium=10)

Experimental conditions: T=100-130° C., p=1.0-2.0 MPa, τ=26-28 secs, $H_2:CO=1$, Volume flow$_{isobutene}$=1.8-3.5 ml min$^{-1}$, Volume flow$_{H2}$=Volume flow$_{CO}$=6.8-8.3 ml min$^{-1}$, $m_{SILP}$=3.0 g, $m_{Rh}$=0.2%, L/Rh=10, $α_{IL}$=10 vol. % (IL=[EMIM[[NH$_2$]).

However from the course of the curve, it must be assumed that the excess of ligand was gradually degraded within the first 55 hrs. In experiment 5, the reaction pressure was raised from 1.0 to 2.0 MPa. Thereby the conversion could be raised briefly from 2.5% to 10%, however, the SILP catalyst system deactivated further.

If the turnover frequency (TOF) at 20% initial conversion is considered, then a value of 287 hr$^{-1}$ is obtained. The space-time yield (abbreviation STY) corresponds to 0.09 kgl cat$^{-1}$ hr$^{-1}$ and the gas hourly space velocity (abbreviation GHSV) to 5.0 llcat$^{-1}$ hr$^{-1}$. In Experiment 6, in the preparation of the SILP catalyst system, the mole ratio of ligand to rhodium was increased to 20:1; URh=20 beforehand. Should the deactivation now proceed more slowly or set in later than in the preliminary experiment with L/Rh=10, then it must be assumed that the ligand was degraded.

TABLE 2

Hydroformylation of isobutene with Rh-2,4-di-t-Bu triphenylphosphite SILP catalyst system

| Expt. | T/° C. | p/MPa | τ/sec | X/% | TOF/ $hr^{-1}$ | n/iso sel./% | STY/ $kgl_{cat}^{-1}hr^{-1}$ | GHSV/ $ll_{cat}^{-1}hr^{-1}$ |
|---|---|---|---|---|---|---|---|---|
| 6 | 100 | 1.0 | 28 | 18.63 | 283.3 | 99.9 | 0.08 | 4.5 |
| 7 | 100 | 1.5 | 42 | 39.51 | 599.1 | 99.9 | 0.17 | 6.3 |
| 8 | 100 | 2.0 | 56 | 28.74 | 436.5 | 99.9 | 0.13 | 3.5 |
| 9 | 100 | 2.5 | 37 | 22.97 | 348.7 | 99.9 | 0.10 | 2.2 |
| 10 | 100 | 2.0 | 35 | 10.55 | 160.2 | 99.8 | 0.05 | 1.3 |
| 11 | 110 | 1.0 | 20 | 9.75 | 443.8 | 99.8 | 0.13 | 7.2 |
| 12 | 120 | 1.0 | 15 | 6.22 | 472.0 | 99.7 | 0.14 | 7.9 |
| 13 | 130 | 1.0 | 15 | 3.34 | 253.8 | 99.5 | 0.07 | 4.3 |

Experimental conditions: T = 100-130° C., p = 1.0-2.5 MPa, τ = 15-56 secs, $H_2:CO = 1$, Volume flow$_{isobutene}$ = 1.3-17.6 ml min$^{-1}$, Volume flow$_{H2}$ = Volume flow$_{CO}$ = 3.5-7.6 ml min$^{-1}$, $m_{SILP}$ = 3.0 g, $m_{Rh}$ = 0.2%, L/Rh = 20, $α_{IL}$ = 10 vol. % (IL = [EMIM][NTf$_2$]).

In Experiment 6 at 100° C. and 10 bar and a residence time of 28 secs with the same settings as in the preliminary experiment, the activity was somewhat lower than in the comparative experiment with an L/Rh ratio of 10. The conversion here corresponds to 18.6% in contrast to 20.7%.

As regards the optimization of the conversion, in Experiment 7 the reaction pressure was increased to 1.5 MPa. Thereby a conversion of 40% was achieved. This increase in the conversion is attributable firstly to the longer residence time of 42 secs, and to higher activity of the catalyst at higher pressures.

In Experiment 8, the catalyst loses activity markedly. Even an increase in the pressure to 2.5 MPa (Experiment 9) brought no improvement. Presumably at the higher conversions of more than 40% there is product concentration in the ionic liquid. Through the increase in the volume flow of synthesis gas, the excess product is stripped out of the ionic liquid in Experiments 9-10.

Figure 6:
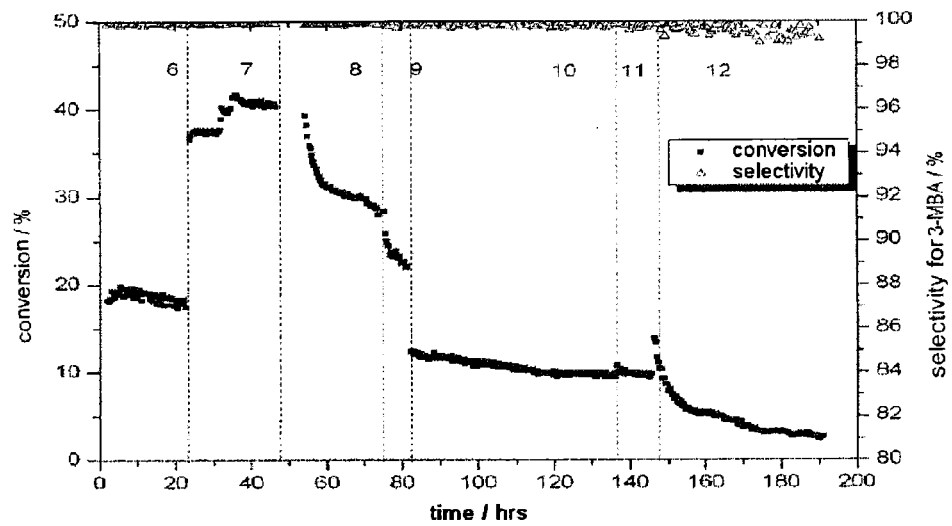
FIG. 6 shows hydroformylation of isobutene with Rh-2,4-di-t-Bu triphenylphosphite SILP catalyst system (ligand/rhodium =20).

Illustration 6 Corresponds to FIG. 6

Illustration 6. Hydroformylation of isobutene with Rh-2,4-di-t-Bu triphenylphosphite SILP catalyst system (ligand/rhodium=20)
Experimental conditions: T=100-130° C., p=1.0-2.5 MPa, τ=15-56 secs, $H_2$:CO=1, Volume flow$_{isobutene}$=1.3-17.6 ml min$^{-1}$, Volume flow$_{H2}$=Volume flow$_{CO}$=3.5-7.6 ml min$^{-1}$, $m_{SILP}$=3.0 g, $m_{Rh}$=0.2%, L/Rh=20, $α_{IL}$=10 vol. % (IL=[EMIM][NTf$_2$]).

If Experiments 6-9 are compared with Experiment 10, then the SILP catalyst system loses almost half of its activity (conversion: 18.8% to 12.5%) within the first 80 hrs. In Experiment 10, the activity slowly reduces over 55 hrs with the same setting. Presumably the ligand is continuously degraded over the whole period due to introduction of water.

In Experiments 11, 12 and 13, attempts were again made to increase the STY or the GHSV by increasing the partial pressure of isobutene. An effect is seen at 145 hrs, where the conversion briefly increases and thereafter falls markedly. Here once again there is product concentration. This was also seen after the removal of the SILP catalyst system from the reactor. If the losses of activity in Experiments 6 and 10 are considered alongside 8 and 12, then this also points to two different phenomena (6 and 10: ligand degradation; 8 and 12: product accumulation). The selectivity decreases in the course of the experiment from 99.9% to 99.5%. By-products such as long-chain alcohols, for example, formed by aldol condensation, could not be detected.

Product concentration in the removed SILP catalyst system could be detected after the experiment by gas chromatography. The SILP catalyst was washed several times with methanol and the combined solution investigated by gas chromatography, 3-MBA being detected.

As a conclusion, it can be stated that the increase in the mole ratio of ligand to rhodium from 10:1 to 20:1 is not sufficient for obtaining a long-term stable SILP catalyst system in the hydroformylation of isobutene.

In the subsequent experiments, in the preparation of the SILP catalyst systems the L/Rh ratio was increased to 40:1, in order to slow the ligand degradation with a marked excess of ligand.

TABLE 3

Hydroformylation of isobutene with Rh-2,4-di-t-Bu triphenylphosphite SILP catalyst system

| Expt. | T/ °C. | p/ MPa | τ/ sec | X/ % | TOF/ hr$^{-1}$ | n/iso sel./% | STY/ kgl$_{cat}^{-1}$hr$^{-1}$ | GHSV/ ll$_{cat}^{-1}$hr$^{-1}$ |
|---|---|---|---|---|---|---|---|---|
| 14 | 130 | 2.0 | 27 | 34.98 | 627.0 | 99.9 | 0.15 | 4.5 |
| 15 | 130 | 2.0 | 26 | 29.36 | 1578.9 | 99.8 | 0.38 | 11.4 |
| 16 | 130 | 2.0 | 22 | 20.93 | 1125.5 | 99.8 | 0.27 | 8.2 |
| 17 | 130 | 2.0 | 19 | 9.15 | 820.3 | 99.7 | 0.20 | 5.9 |

Experimental conditions: T = 130° C., p = 2.0 MPa, τ = 19-27 secs, $H_2$:CO = 1, Volume flow$_{isobutene}$ = 1.7-8.8 ml min$^{-1}$, Volume flow$_{H2}$ = Volume flow$_{CO}$ = 6.7-8.2 ml min$^{-1}$, $m_{SILP}$ = 3.0 g, $m_{Rh}$ = 0.2%, L/Rh = 40, $α_{IL}$ = 10 vol. % (IL = [EMIM][NTf$_2$]).

This series of experiments was started with 2.0 MPa and 130° C. Thereby the SILP catalyst system already reached a conversion between 35% at the start. The activity falls at the start because of the high conversions and the product concentration in the SILP phase resulting from this.

Figure 7:
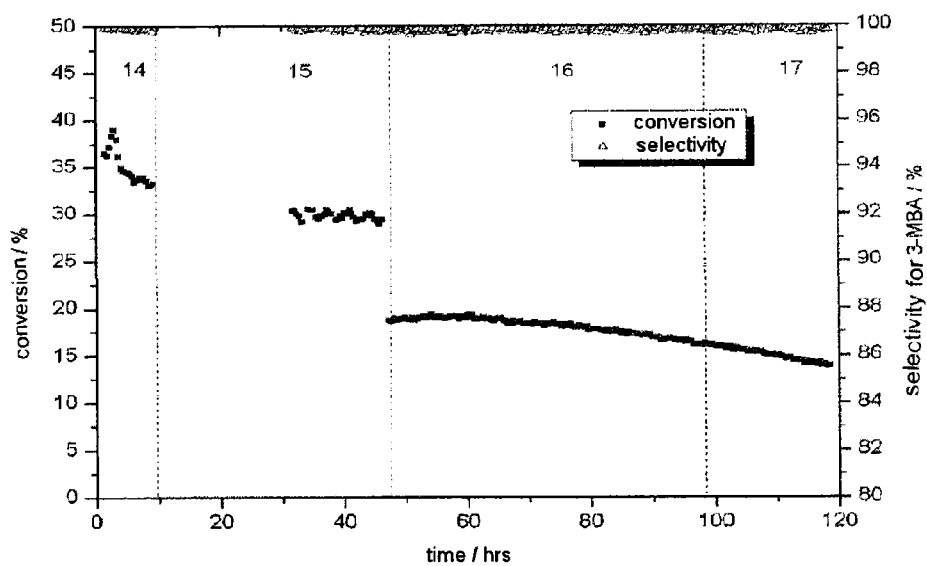
FIG. 7 shows hydroformylation of isobutene with Rh-2,4-di-t-Bu triphenylphosphite SILP catalyst system (ligand/rhodium =40)

Illustration 7 Corresponds to FIG. 7

Illustration 7. Hydroformylation of isobutene with Rh-2,4-di-t-Bu triphenylphosphite SILP catalyst system (ligand/rhodium=40)
Experimental conditions: T=130° C., p=2.0 MPa, τ=19-27 secs, $H_2$:CO=1, Volume flow$_{isobutene}$=1.7-8.8 ml min$^{-1}$, Volume flow$_{H2}$=Volume flow$_{CO}$=6.7-8.2 ml min$^{-1}$, $m_{SILP}$=3.0 g, $m_{Rh}$=0.2%, L/Rh=40, $α_{IL}$=10 vol. % (IL=[EMIM[[NTf$_2$]).

In Experiment 15, with the residence time remaining the same, the partial pressure or the volume flow of isobutene was tripled. As a result, in comparison to section 14 very high STY or GHSV could be achieved. Under these conditions, the STY was 0.38 kglcat$^{-1}$ hr$^{-1}$ and the GHSV 11.4 llcat$^{-1}$ h$^{-1}$. During the whole experiment, the selectivity remained between 99.9 and 99.7% for 3-MBA. Over 15 hrs in this section a constant conversion of 30% could be achieved.

In the penultimate section, the volume flow of isobutene was once again increased, as a result of which the activity began to fall after 60 hrs. The deactivation rate is very low, but nonetheless indicates ligand degradation, such as was already described in the preliminary experiments. For plant engineering reasons, the experiment had to be terminated after 120 hrs.

Overall, the increase in the ligand excess leads to a more stable SILP catalyst system, which nonetheless still slowly deactivates. Consequently the attempt was made by means of a so-called guard bed to reduce possible contamination with water, which leads to degradation of the ligand or hydrolysis thereof and to deactivation of the hydroformylation. The guard bed filling was introduced into the fixed bed reactor before the SILP catalyst system and consisted of silicon dioxide [Silica 100, Merck]. This was coated with 2,4-di-t-Bu triphenylphosphite in order to trap water before it reaches the SILP catalyst system. For comparison the experiment was performed with no guard bed.

TABLE 4

Hydroformylation of isobutene with Rh-2,4-di-t-Bu triphenylphosphite SILP catalyst system with the use of a guard bed (Silica 100: 2.66 g; 2,4-di-t-Bu triphenylphosphite: 1.34 g)

| Expt. | Guard Bed | T/ °C. | p/ MPa | τ/ sec | X/ % | TOF/ hr$^{-1}$ | n/iso sel./% | STY/ kgl$_{cat}^{-1}$hr$^{-1}$ | GHSV/ ll$_{cat}^{-1}$ ihr$^{-1}$ |
|---|---|---|---|---|---|---|---|---|---|
| 18 | Yes | 100 | 4.0 | 71 | 78.9[2] | 1412 | 99.9 | 0.34 | 4.7 |
| 19 | No | 100 | 4.0 | 71 | 75.2[3] | 1346 | 99.9 | 0.3 | 4.5 |

[2]Average activity for the first 10 hrs operating time, since the catalyst deactivates markedly.
[3]Average activity for the first 10 hrs operating time, since the catalyst deactivates markedly.
Experimental conditions: T = 100° C., p = 4.0 MPa, τ = 71 secs, $H_2$:CO = 1, Volume flow$_{isobutene}$ = 0.8 ml min$^{-1}$, Volume flow$_{H2}$ = Volume flow$_{CO}$ = 30 ml min$^{-1}$, $m_{SILP}$ = 3.0 g, $m_{Rh}$ = 0.2%, L/Rh = 10, $α_{IL}$ = 10 vol. % (IL = [EMIM][NTf$_2$]).

At the start, a reaction pressure of 4.0 MPa and a temperature of 100° C. were set. Furthermore, the residence time was increased to 71 secs. As a result, at the start, in the first section, maximal conversions up to 85% could be achieved. However, the conversion fell markedly again in the course of the experiment, since once again product concentration occurred. This could be confirmed by a vacuum phase for 10 hrs after 95 hrs, since an increase in the conversion from 50% to 70% could briefly be discerned. During the vacuum phase, product and high boilers were removed from the ionic liquid. (See Illustration 8). After a short time, the conversion again fell to the initial deactivation rate. After 120 hrs, the catalyst possessed only half of its activity of 41% conversion. The deactivation rate corresponds to that in Experiment 8, hence this guard bed can neither prevent nor retard the loss of activity. It should be considered whether another drying agent should be used as a guard bed, such as for example calcium fluoride, so as to be able to completely rule out deactivation with $H_2O$.

In a further experiment, it could be seen that likewise no success could be obtained with the aid of helium as an inert stream which was introduced in addition to the isobutene and synthesis gas stream in order to dilute the feed or to strip the catalyst. Raising the reaction temperature or reaction pressure also did not counteract the deactivation.

The selectivity for 3-MBA during the experiments remained constant at over 99.7%. By-products in this experiment only appeared towards the end, since owing to the product accumulation aldol condensation occurred and longer-chain alcohols were formed. However, the quantity was very small and amounted to less than <1% of the total products.

Figure 8:
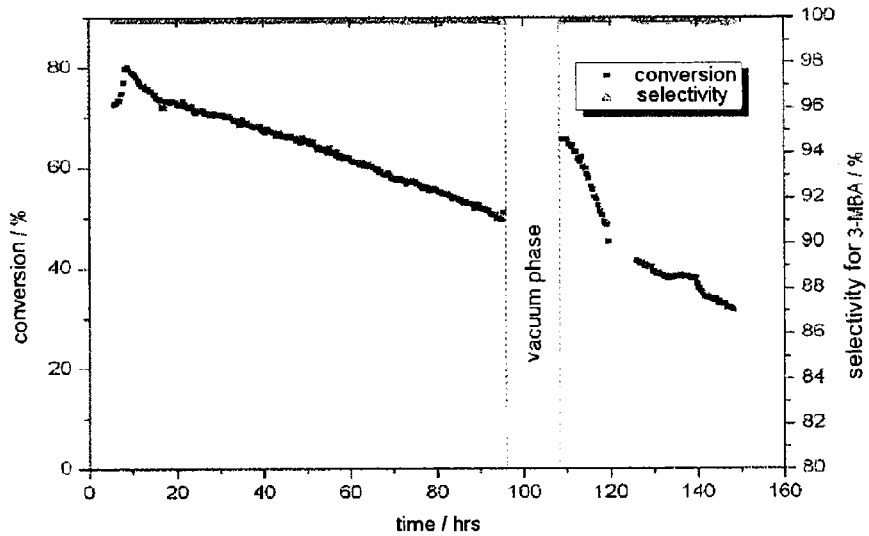
FIG. 8 shows an effect of the vacuum phase in the hydroformylation of isobutene.

Illustration 8 Corresponds to FIG. 8

Illustration 8. Effect of the vacuum phase in the hydroformylation of isobutene.
Experimental conditions: T=140° C., p=4.0 MPa, τ=71 secs, $H_2$:CO=1, Volume flow$_{isobutene}$=0.82 ml min$^{-1}$, Volume flow$_{H2}$=Volume flow$_{CO}$=3.0 ml min$^{-1}$, m$_{SILP}$=3.0 g, m$_{Rh}$=0.2%, L/Rh=10, α$_{IL}$=10 vol. % (IL=[EMIM][NTf$_2$]).

As a third modification for maintenance of the hydroformylation activity, organic amines (abbreviation OA) were for the first time used in the SILP catalyst system according to Example 1. The organic amine OA used, such as for example bis(2,2,6,6-tetramethyl-4-piperidyl)sebacate, inter alia prevents or retards the hydrolytic decomposition of the ligand. The action of these organic amines OA for the protection of polymers against short wavelength radiation, for example UV radiation, has previously been described, as is also shown for bis(2,2,6,6-tetramethyl-4-piperidyl)sebacate. As part of the SILP catalyst system, the organic amines OA react with the phosphoric acid derivatives that form, which arise from the ligand degradation by water. As a result, the concentration of phosphoric acid derivatives and the formation of further phosphoric acid derivatives through autocatalysis decrease at the same time. Thus in the presence of water the catalytic destructive action of the phosphoric acid derivatives on the ligands can be avoided. Further degradation reactions of phosphite ligands are shown in Scheme 2. Transesterification, O—C cleavage, O—P cleavage and side-reactions with the aldehyde formed, e.g. aldol condensations and acetalizations also occur.

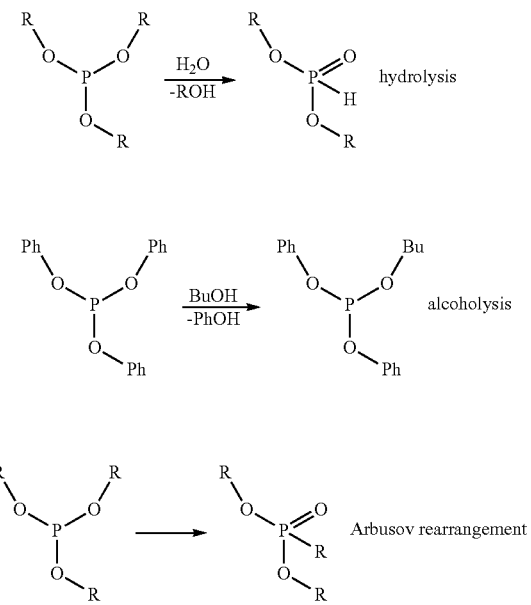

Scheme 2. Possible side-reactions which lead to ligand degradation

Figure 9:
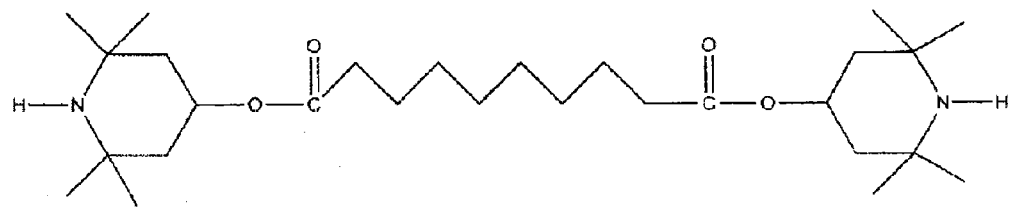
FIG. 9 shows a chemical structure of organic amine OA used: bis(2,2,6,6-tetramethyl-4-piperidyl)sebacate.

Illustration 9 Corresponds to FIG. 9

Illustration 9. Organic amine OA used: bis(2,2,6,6-tetramethyl-4-piperidyl)sebacate The experiments were performed with a molar OA to ligand ratio of 4. In the experiments with addition of the organic amine OA, attempts were made to increase the long term stability with lower volume flows of isobutene and lower conversions due to lower reaction pressure and temperature.

TABLE 5

Hydroformylation of isobutene with Rh-2,4-di-t-Bu triphenylphosphite SILP catalyst system with the use of an organic amine OA

| Expt. | T/° C. | p/MPa | τ/sec | X/% | TOF/hr$^{-1}$ | n/iso sel./% | STY/ kgl$_{cat}^{-1}$hr$^{-1}$ | GHSV/ ll$_{cat}^{-1}$hr$^{-1}$ | Stability/ hr |
|---|---|---|---|---|---|---|---|---|---|
| 20 | 100 | 1.0 | 28.1 | 9.03 | 105.0 | 99.8 | 0.04 | 2.2 | 90 |
| 21 | 150 | 1.0 | 28.1 | 2.15 | 25.0 | 98.0 | 0.01 | 0.6 | 5 |
| 22 | 100 | 1.0 | 28.1 | 8.80 | 102.7 | 99.8 | 0.04 | 2.2 | 67 |
| 23 | 100 | 1.0 | 28.1 | 2.54 | 102.7 | 99.8 | 0.03 | 1.8 | 7 |
| 24 | 100 | 1.0 | 28.1 | 8.77 | 102.3 | 99.8 | 0.04 | 2.2 | 16 |
| 25 | 100 | 2.0 | 28.1 | 34.11 | 398.0 | 99.8 | 0.15 | 4.1 | 14 |
| 26 | 100 | 2.5 | 28.1 | 37.30 | 1740 | 99.9 | 0.65 | 14.4 | —[4] |

[4]Catalyst begins to lose activity
Experimental conditions: T = 100-150° C., p = 1.0-2.5 MPa, τ = 28.1 secs, $H_2$:CO = 1, Volume flow$_{isobutene}$ = 1.6-9.8 ml min$^{-1}$, Volume flow$_{H2}$ = Volume flow$_{CO}$ = 3.9-7.9 ml min$^{-1}$, m$_{SILP}$ = 3.0 g, m$_{Rh}$ = 0.2%, L/Rh = 10, OA/L = 4, α$_{IL}$ = 10 vol. % (IL = [EMIM][NTf$_2$]).

Figure 10:
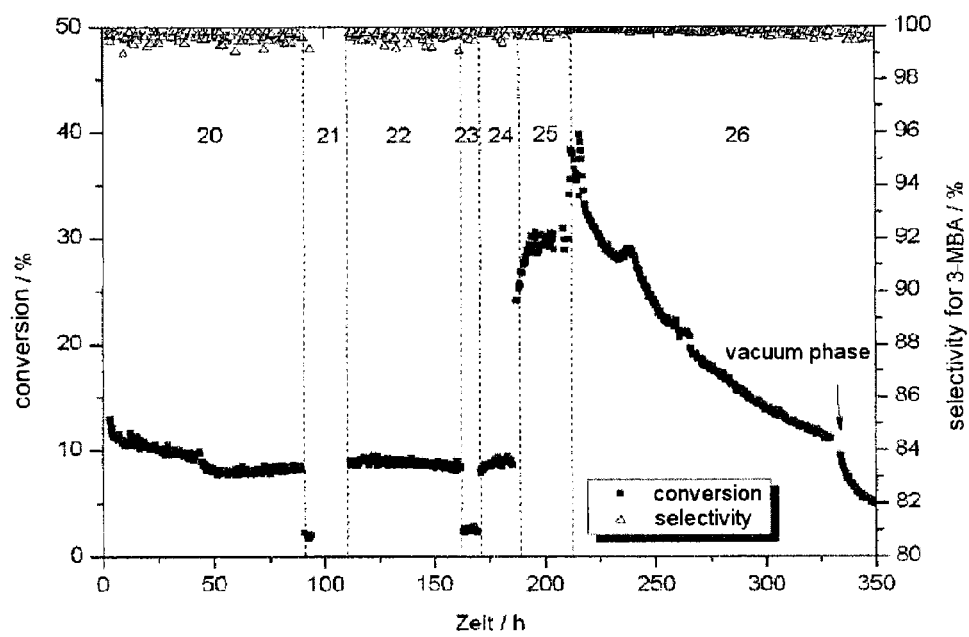
FIG. 10 shows hydroformylation of isobutene with Rh-2,4-di-t-Bu triphenylphosphite SILP catalyst system with the use of an organic amine OA.

Illustration 10 Corresponds to FIG. 10

Illustration 10. Hydroformylation of isobutene with Rh-2,4-di-t-Bu triphenylphosphite SILP catalyst system with the use of an organic amine OA
Experimental conditions: T=100-150° C., p=1.0-2.5 MPa, τ=28.1 secs, $H_2$:CO=1, Volume flow$_{isobutene}$=1.6-9.8 ml min$^{-1}$, Volume flow$_{H2}$=Volume flow$_{CO}$=3.9-7.9 ml min$^{-1}$, m$_{SLIP}$=3.0 g, m$_{Rh}$=0.2%, L/Rh=10, OA/L=4, α$_{IL}$=10 vol. % (IL=[EMIM][NTf$_2$]).

In Experiment 20, the conversion fell from 13% to 9% within 50 hrs. Beyond an experiment run time of 50 hrs, the conversion now remained constant at 9% up to a reaction period of 180 hrs. Because of the organic amine OA used and the lower conversions, there seems to be no ligand degradation or less product concentration. The selectivity for 3-MBA during the 180 hrs was on average 99.8%.

In Experiment 21, the behaviour of the catalyst at 150° C. was briefly tested. The result of the temperature increase was a decrease in the conversion to 2%. Such behaviour is in contrast to the expected Arrhenius behaviour and can only be explained by flooding of the pore network by product, or poorer solubility of the substrate at higher temperatures. In the following Experiment 22, the initial conditions were again set, whereupon the catalyst fully reactivated and again yielded the initial 9% conversion.

In Experiment 23, the attempt was made to increase the GHSV or the STY through a high volume flow of isobutene. However, the conversion once again fell to 2%, whereupon the initial settings were again adopted. Here also, the initial conversion could be achieved.

In Experiments 25 and 26, the attempt was now made to raise the activity of the SILP catalyst system by variation of the pressure. A first increase in the pressure to 2.0 MPa brought an increase in conversion from 9% to 34%, which could be maintained constant for 20 hrs. An increase in the pressure to 2.5 MPa once again led to an increase in the conversion to 37%, however, the catalyst began to deactivate as a result. A vacuum phase at 330 hrs brought no reactivation of the system. Nonetheless, at 220 hrs, the SILP catalyst system with organic amine OA in the gas phase hydroformylation of isobutene is markedly more stable than experiments without addition thereof.

The high dependence on pressure with use of the ligand of the formula IX, 2,4-di-t-Bu triphenylphosphite must be emphasized. With a slight increase in the total pressure, very high conversions can already be achieved, which however lead to product accumulation in the ionic liquid IL.

TABLE 6

Pressure dependence of the Rh-2,4-di-t-Bu triphenylphosphite SILP catalyst system with the use of an organic amine OA

| Expt. | T/ ° C. | p/ MPa | τ/ sec | X/ % | TOF/ hr$^{-1}$ | n/iso sel./% | STY/ kgl$_{cat}^{-1}$hr$^{-1}$ | GHSV/ ll$_{cat}^{-1}$hr$^{-1}$ |
|---|---|---|---|---|---|---|---|---|
| 27 | 100 | 1.0 | 70.1 | 34.16 | 389.5 | 99.9 | 0.15 | 8.2 |
| 28 | 100 | 2.0 | 70.1 | 49.76 | 580.5 | 99.9 | 0.22 | 5.6 |
| 29 | 100 | 3.0 | 70.1 | 71.31 | 831.9 | 99.9 | 0.31 | 5.7 |
| 30 | 100 | 4.0 | 70.1 | 73.19 | 853.9 | 99.9 | 0.32 | 4.4 |
| 31 | 100 | 5.0 | 70.1 | 75.94 | 886.0 | 99.9 | 0.33 | 3.7 |

Experimental conditions: T = 100° C., p = 1.0-5.0 MPa, τ = 70.1 secs, H$_2$:CO = 1, Volume flow$_{isobutene}$ = 0.7-3.3 ml min$^{-1}$, Volume flow$_{H2}$ = Volume flow$_{CO}$ = 1,-3.2 ml min$^{-1}$, m$_{SILP}$ = 3.0 g, m$_{Rh}$ = 0.2%, L/Rh = 10, OA/L = 4, α$_{IL}$ = 10 vol. % (IL = [EMIM][NTf$_2$]).

On consideration of Table 6, two different sections in the increase in the conversion are discerned. Between 1.0 and 3.0 MPa the conversion doubles from 35% at 1.0 MPa to 71% at 3.0 MPa. Thereafter, between 3.0 mPa and 5.0 mPa hardly any further increase in the activity can be discerned. The conversion rises further up to 75% at 5.0 mPa. The selectivity for 3-MBA remains constant at about 99.5%.

Operating an SILP catalyst system with undiluted substrate and high conversions inevitably results in product becoming concentrated in the ionic liquid IL. As a result, the quantity of substrate in the IL decreases and consequently the conversion falls. With low conversions and low substrate contents, the SILP catalyst system with the use of an organic amine OA in the gas phase hydroformylation of isobutene can be operated with long-term stability (see Illustration 10, Experiments 20-24).

Example 8

Experimental Series for the Hydroformylation of Propene

In addition, the long-term stability of these SILP catalyst systems is of interest for the hydroformylation of ethene and propene with the phosphorus-containing organic ligands L of the formulae VII and VIII. In prior thermogravimetric measurements, the thermal stability of the SILP catalyst systems was studied and found to be stable up to at most 150° C. For certainty, the stability experiments were run at 120° C. reaction temperature.

Figure 11:
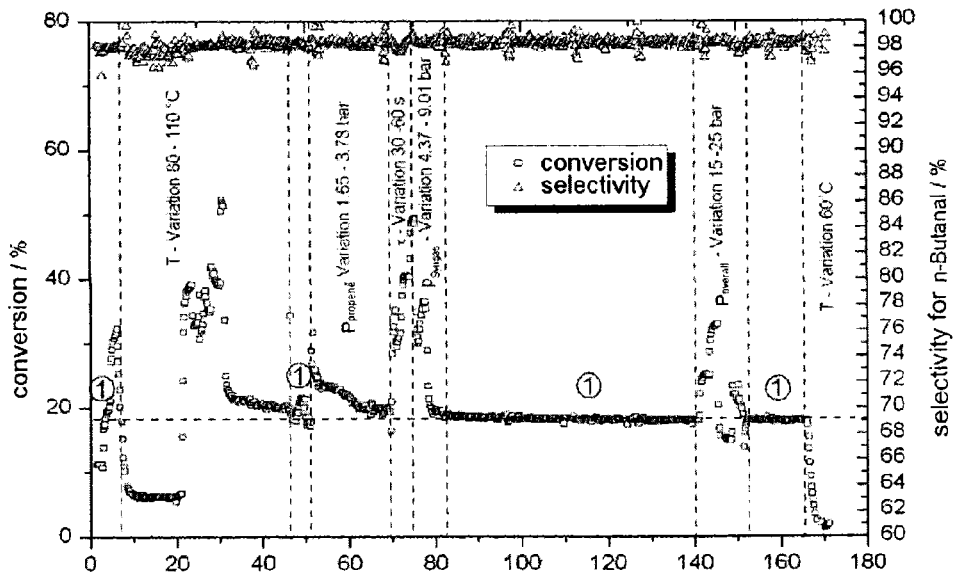
FIG. 11 shows a long-term stability of the propene hydroformylation during 170 hours of operation with the use of the ligand VIII in the SILP catalyst system.

Illustration 11 Corresponds to FIG. 11

Illustration 11. Long-term stability of the propene hydroformylation during 170 hours of operation with the use of the ligand VIII in the SILP catalyst system
Experimental conditions: T=60-110° C., p=1.5-2.5 MPa, τ=24-60 secs, H2:CO=0.8-1.2, Volume flow$_{propene}$=1.2-5.4 ml min$^{-1}$, Volume flow$_{H2}$=Volume flow$_{helium}$=2.3-10.0 ml min$^{-1}$, Volume flow$_{helium}$=1.4-4.0 ml min$^{-1}$
m$_{SILP}$=1.88 g, m$_{Rh}$=0.2%, L/Rh=10, OA/L=4, α$_{IL}$=10 vol. % (IL=[EMIM][NTf$_2$]).
Reference conditions 1: T=92° C., p=1.5 MPa, τ=30 secs, H$_2$:CO=1, $\dot{V}_{propene}$=2.6 ml min$^{-1}$, $\dot{V}_{H2}$=$\dot{V}_{CO}$=7.6 ml min$^{-1}$, $\dot{V}_{helium}$=3.10 ml min$^{-1}$.

In order to investigate the stability of the SILP catalyst system used, the reference conditions 1 were repeated during the experiments at defined time intervals.

In Illustration 11, the total run time of the propene hydroformylation with the ligand VIII in the SILP catalyst system is shown. During the 170 hr experiment duration, different parameters were varied. It is evident that during the 170 hrs the SILP catalyst system does not lose activity and with the same reference conditions 1 yields identical conversion. The selectivity for linear butanal is constant at over 98%. For this experiment the GHSV are at most 25.94 llcat$^{-1}$ hr$^{-1}$, the STY about 0.52 kglcat$^{-1}$ hr$^{-1}$ and the TOF about 2982 hr$^{-1}$. The maximum conversion is about 48.3%.

In the following Illustration 12, the experiment series on the long-term stability of the propene hydroformylation with the ligand of the formula VII in the SILP catalyst system is shown.

Figure 12:
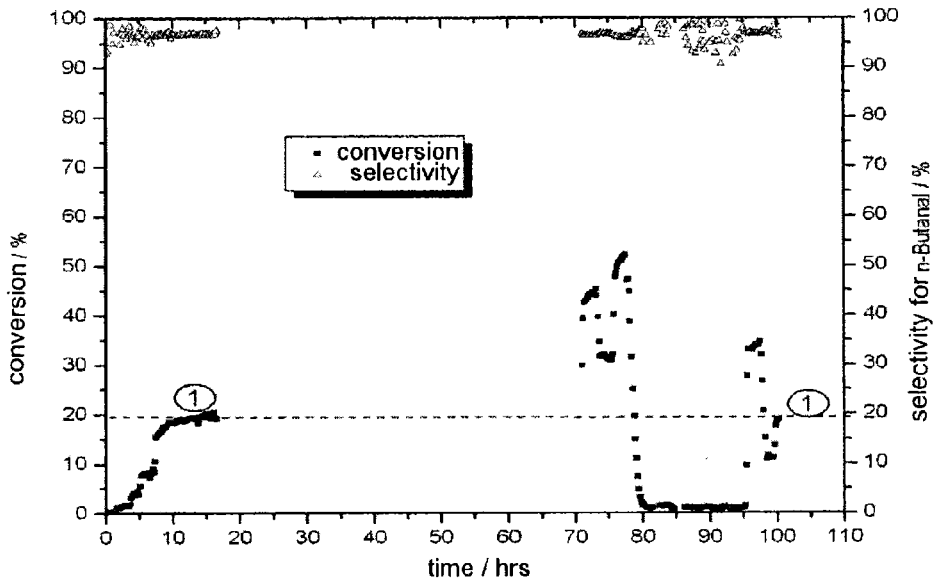
FIG. 12 shows a long-term stability of propene hydroformylation with the use of the ligand VII in the SILP catalyst system over 100 hours of operation.

Illustration 12 Corresponds to FIG. 12

Illustration 12. Long-term stability of propene hydroformylation with the use of the ligand VII in the SILP catalyst system over 100 hours of operation
Experimental conditions: T=60-125° C., p=1.5 MPa, τ=30 secs, H$_2$:CO=1,
Volume flow$_{propene}$=2.3-2.8 ml min$^{-1}$, Volume flow$_{H2}$=Volume flow$_{CO}$=7.2-7.9 ml min$^{-1}$,
Volume flow$_{helium}$=2.8-3.4 ml min$^{-1}$,
m$_{SILP}$=1.88 g, m$_{Rh}$=0.2%, L/Rh=10, OA/L=4, α$_{IL}$=10 vol. % (IL=[EMIM][NTf$_2$]).
Reference conditions 1: T=92° C., p=1.5 MPa, τ=30 secs, H$_2$:CO=1, $\dot{V}_{propene}$=2.6 ml min$^{-1}$, $\dot{V}_{H2}$=$\dot{V}_{CO}$=9.0 ml min$^{-1}$, $\dot{V}_{helium}$=3.2 ml min$^{-1}$.

Once again various parameters were varied, whereby the conversion and the selectivity for n-butanal, at the start as also at the end of the experimental series, with setting of the reference conditions 1, exhibit values which were already previously achieved with the use of the ligand of the formula VIII.

Example 9

Experimental Series for the Hydroformylation of Ethene

Figure 13:
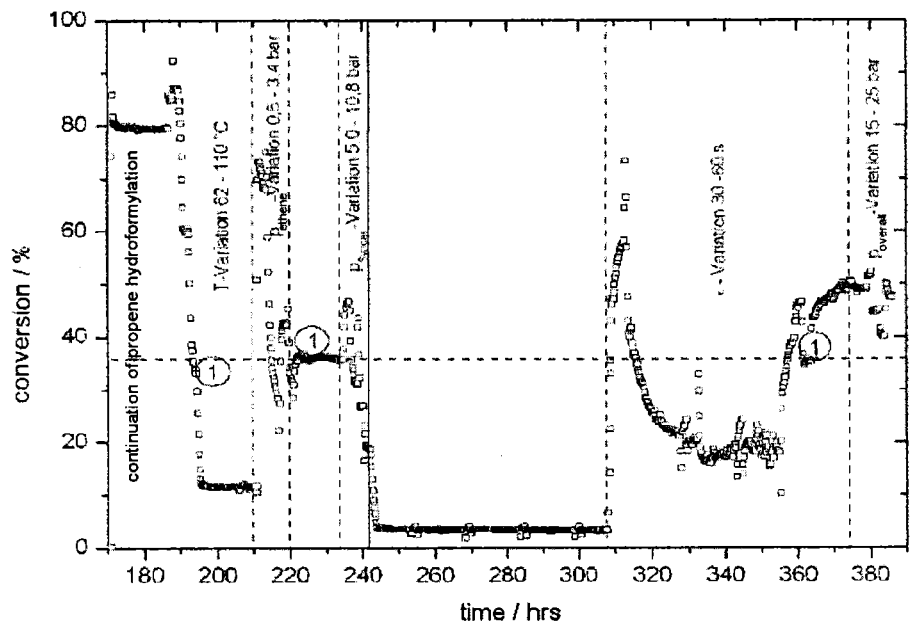
FIG. 13 shows a long-term stability of ethene hydroformylation during 215 hours of operation with the use of the ligand VIII in the SILP catalyst system.

Illustration 13 Corresponds to FIG. 13

Illustration 13. Long-term stability of ethene hydroformylation during 215 hours of operation with the use of the ligand VIII in the SILP catalyst system
Experimental conditions: T=54-110° C., p=1.5-2.5 MPa, τ=30-60 secs, $H_2$:CO=0.65-1.2,
Volume flow$_{ethene}$=0.5-3.5 ml min$^{-1}$, Volume flow$_{H2}$=Volume flow$_{CO}$=4.5-10.0 ml min$^{-1}$, $m_{SILP}$=1.88 g, $m_{Rh}$=0.2%, L/Rh=10, OA/L=4, $α_{IL}$=10 vol. % (IL=[EMIM][NTf$_2$]). Reference conditions 1: T=72° C., p=1.5 MPa, τ=33 secs, $H_2$:CO=1, $\dot{V}_{ethene}$=0.8 ml min$^{-1}$, $\dot{V}_{H2}$=$\dot{V}_{CO}$=8.9 ml min$^{-1}$.

Illustration 13 shows the whole course (215 hrs) of the ethene hydroformylation with the use of the ligand of the formula VIII in the SILP catalyst system which was already tested in the propene hydroformylation for 170 hrs. During the experiment, temperature, residence time and pressure or partial pressures were varied in order to determine the formal kinetics of the catalyst with ethene. Through the repeated setting of the reference conditions 1 and the conversion remaining constant, deactivation of the catalyst after a total of 380 hrs could be ruled out. For this experiment, the GHSV were at most 28.5 llcat-1 h-1, the STY about 0.42 kglcat-1 hr-1 and the TOF about 3600 hr-1. The maximum constant conversion is about 84.4%.

In the following Illustration 14, the experimental series on the long-term stability of the ethene hydroformylation with the ligand of the formula VII in the SILP catalyst system is shown.

Figure 14:
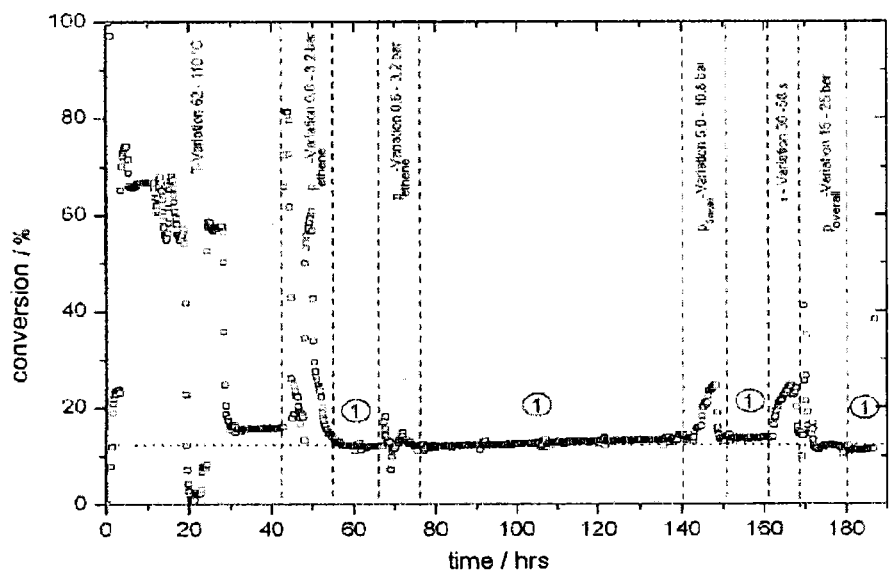
FIG. 14 shows a long-term stability of the ethene hydroformylation with the use of the ligand VII in the SILP catalyst system over 190 hours of operation.

Illustration 14 Corresponds to FIG. 14

Illustration 14. Long-term stability of the ethene hydroformylation with the use of the ligand VII in the SILP catalyst system over 190 hours of operation
Experimental conditions: T=62-110° C., p=1.5-2.5 MPa, τ=30-57 secs, $H_2$:CO=1, Volume flow$_{ethene}$=0.8-3.8 ml min$^{-1}$, Volume flow$_{H2}$=Volume flow$_{CO}$=4.8-9.3 ml min$^{-1}$, 1.88 g, $m_{Rh}$=0.2%, L/Rh=10, OA/L=4, $α_{IL}$=10 vol. % (IL=[EMIM][NTf$_2$]).
Reference conditions 1: T=87° C., p=1.5 MPa, τ=30 secs, $H_2$:CO=1, $\dot{V}_{ethene}$=2.5 ml min$^{-1}$, $\dot{V}_{H2}$=$\dot{V}_{CO}$=9.1 ml min$^{-1}$.

The variation of the experimental parameters after a 190 hr duration with repeated setting of the reference conditions 1 once again yields the values achieved at the beginning as regards the conversion and is evidence for the long-term stability of the SILP catalyst system with the ligand VII.

Example 10

Experimental Series for the Hydroformylation of 1-Butene

Figure 15:
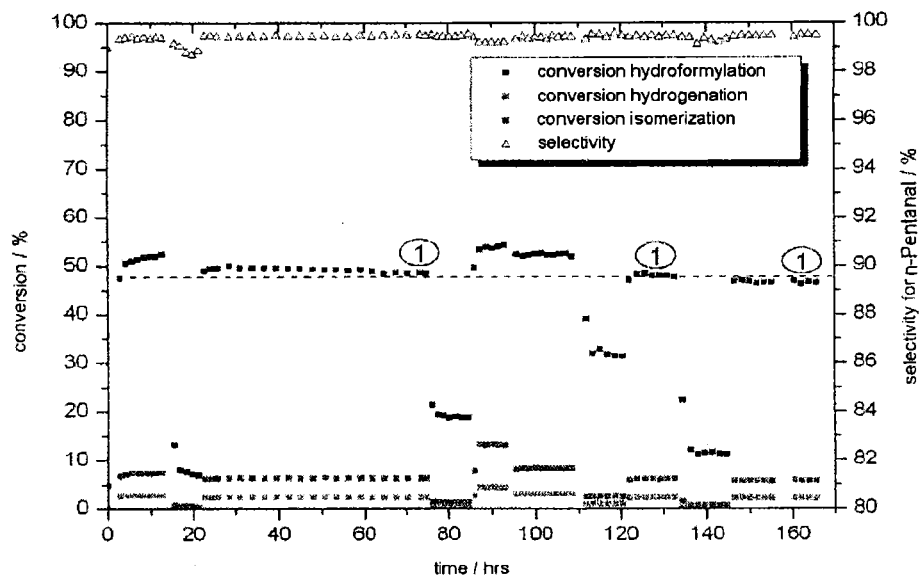
FIG. 15 shows a long-term stability of the 1-butene hydroformylation during 166 hours of operation with the use of the ligand VIII in the SILP catalyst system.

Illustration 15 Corresponds to FIG. 15

Illustration 15. Long-term stability of the 1-butene hydroformylation during 166 hours of operation with the use of the ligand VIII in the SILP catalyst system
Experimental conditions: T=60-120° C., p=1.0 mPa, τ=16 secs, $H_2$:CO=1, Volume flow$_{1\text{-}butene}$=3.2-395 ml min$^{-1}$, Volume flow$_{H2}$=Volume flow$_{CO}$=12.2-14.4 ml min$^{-1}$, $m_{SILP}$=3.0 g, $m_{Rh}$=0.2%, L/Rh=10, OA/L=4, $α_{IL}$=10 vol. % (IL=[EMIM][NTf$_2$]).

Reference conditions 1: T=105° C., p=1.0 mPa, τ=16 secs, $H_2$:CO=1, $\dot{V}_1$-Buten=3.2 ml $\dot{V}_{H2}$=$\dot{V}_{CO}$=12.2 ml In a period of 166 hours of operation, the hydroformylation of 1-butene with an SILP catalyst system with the use of the ligand of the formula VIII was subjected to temperature variation; see Illustration 15. During this time, the reference conditions 1 were repeatedly set, whereby approximately the same activities and selectivities were achieved. The selectivity for linear n-pentanal is over 99% throughout. In addition to the hydroformylation activity, the hydrogenation and isomerization of the catalyst during the experimental phase were recorded. The conversion of 1-butene which was hydroformylated lies between 8.5% (60° C.) and 53.6% (120° C.). In parallel, the SILP catalyst system hydrogenated between 0.2% (60° C.) and 4.4% (120° C.) of 1-butene to n-butane. The isomerization of 1-butene to 2-butene was 0.5% to 13.1%, the ratio of trans-2-butene to cis-2-butene varying between 1.2 and 3. For this experiment, the GHSV is at most 12.8 llcat$^{-1}$ hr$^{-1}$, the STY about 0.19 kglcat$^{-1}$ hr$^{-1}$ and the TOF about 1128 hr$^{-1}$. The maximal constant conversion is about 53.6%.

The use of the ligand of the formula VII in the SILP catalyst system for the hydroformylation over ca. 190 hrs is shown in the following Illustration 16.

Figure 16:
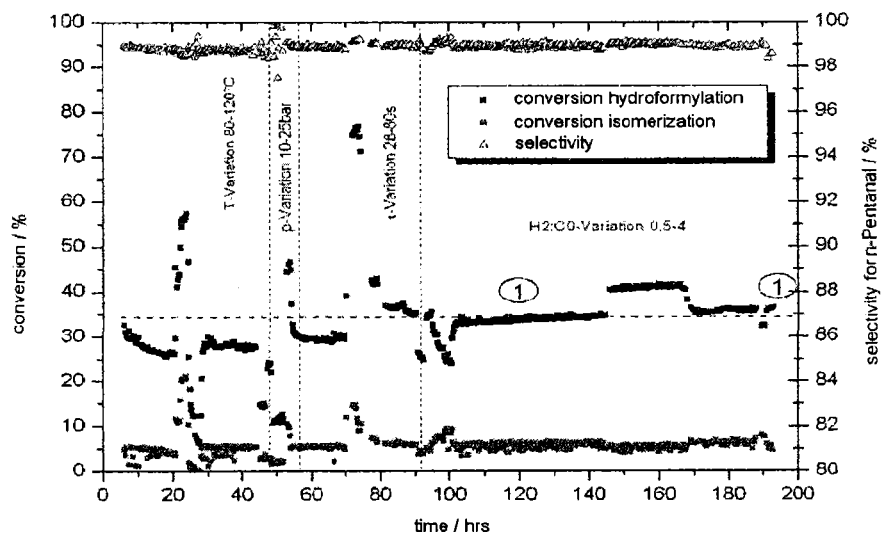
FIG. 16 shows a long-term stability of the 1-butene hydroformylation with the use of the ligand VII in the SILP catalyst system over 190 hours of operation.

Illustration 16 Corresponds to FIG. 16

Illustration 16. Long-term stability of the 1-butene hydroformylation with the use of the ligand VII in the SILP catalyst system over 190 hours of operation
Experimental conditions: T=80-120° C., p=1.0 mPa, τ=27-80 secs, $H_2$:CO=0.5-4.0, Volumeflow$_{1\text{-}butene}$=1.1-3.0 ml min$^{-1}$, Volume flow$_{H2}$=Volume flow$_{CO}$=2.7-11.3 ml min$^{-1}$, Volume flow$_{helium}$=0-17.0 ml min$^{-1}$
$m_{SILP}$=4.02 g, $m_{Rh}$=0.4%, L/Rh=10, $α_{IL}$=10 vol. % (IL=[EMIM][NTf$_2$]).
Reference conditions 1: T=100° C., p=1.0 mPa, τ=39 secs, $H_2$:CO=1, $\dot{V}_1$-Buten=2.8 ml min$^{-1}$, $\dot{V}_{H2}$=$\dot{V}_{CO}$=7.0 ml min$^{-1}$.

The variation of the experimental parameters after a 190 hr duration with repeated setting of the reference conditions 1 once again yields the values achieved at the beginning as regards the conversion and also the selectivity for n-pentanal and the isomerization of 1- to 2-butenes, which is also to be observed with the use of the ligand of the formula VIII. The results presented in Illustration 16 are evidence for the long-term stability of the SILP catalyst system with the ligand of the formula VII.

As a conclusion, the stability data from this experimental series with the ligands used in each case are once again summarized in Table 7.

TABLE 7

| Stability data from the kinetic study | |
|---|---|
| Substrate/Ligand | Stability/hrs |
| ethene/VIII | >214 |
| ethene/VII | >187 |
| propene/VIII | >171 |
| propene/VII | 100 |
| 1-butene/VIII | >166 |
| 1-butene/VII | >193 |

The long-term stability studies, in addition to the thermal stability, indicate stable SILP catalyst systems up to a reaction temperature of 120° C.

Example 11

Experimental Series for the Hydroformylation of Raffinate I

For the first experiments, a raffinate I with a water content of 500 ppm was used in order to test the stability of the SILP catalyst system with the use of the ligand VIII towards this substrate. At temperatures between 80° C. and 100° C. and an overall pressure of 1.0 mPa, the following progressions in the activity and selectivity were plotted against the experiment time.

Figure 17:
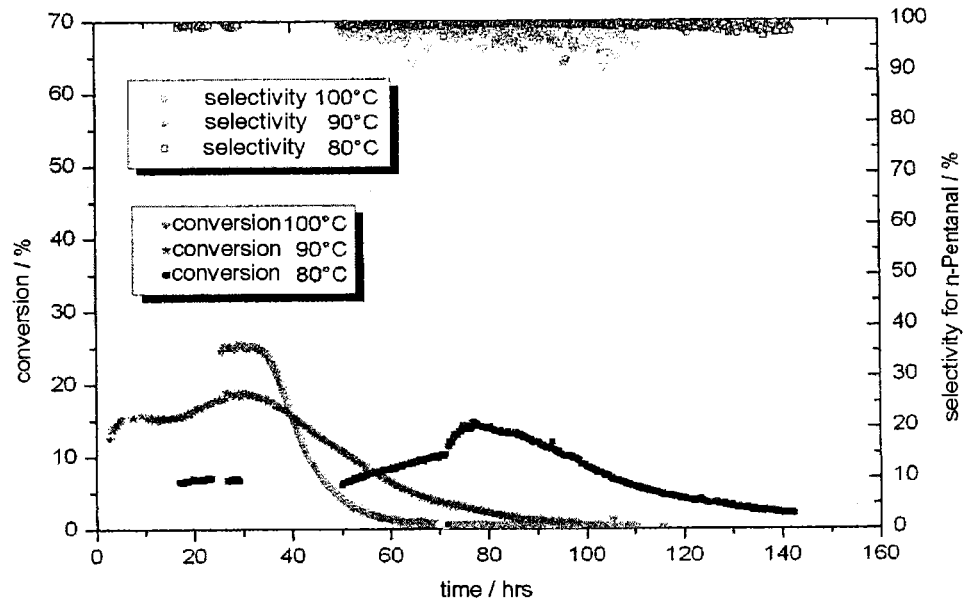
FIG. 17 shows hydroformylation with water-containing raffinate I with the use of the ligand VIII in the SILP catalyst system.

Illustration 17 Corresponds to FIG. 17

Illustration 17. Hydroformylation with water-containing raffinate I with the use of the ligand VIII in the SILP catalyst system
Experimental conditions: T=80-100° C., p=1.0 mPa, τ=29 secs, $H_2$:CO=1, Volume flow$_{raffinate1}$=2.6 ml min$^{-1}$, Volume flow$_{H2}$=Volume flow$_{CO}$=5.6 ml$^{-1}$, $m_{SILP(Rh-L200)}$=3 g, $m_{Rh}$=0.2%, L/Rh=10, $α_{IL}$=10 vol. % (IL=[EMIM][NTf$_2$]).

The activity progression in Illustration 17 shows an activity loss within the 80 hr experiment run time for all three temperatures. The deactivation rate increases with higher temperature. Firstly, after a short activation phase the SILP catalyst system reaches a stable plateau, especially at 80° C. and 90° C. Thereafter, the activity rises to a maximum. In this phase the initial ligand/rhodium ratio decreases continuously from 10 until the activity maximum is reached, where the ratio L/Rh corresponds to 1. The loss of activity then begins. The selectivity for n-pentanal is stable over 98% until the activity maximum is reached. Next, the selectivity gently falls. The branched aldehydes that form are 2-methylbutyraldehyde (2-MBA) and 3-methylbutyraldehyde (3-MBA), depending on the conversion of isobutene (3-MBA) or 2-butenes (2-MBA) in the raffinate I. The maximal conversion based on the butene fraction reached 25% at 100° C., 18% at 90° C. and 14% at 80° C. The butane fraction of the raffinate I is regarded as inert, and is not taken into account in the calculation of the conversion.

In the next experiments, an organic amine OA was used, analogously to Example 7 and the hydroformylation of isobutene. Deviating from the general preparation of the SILP catalyst systems according to Example 1, a minimal OA/L ratio of 1 was at first used. For comparison, the gas phase hydroformylation was performed at 80° C. and 1.0 mPa overall pressure ($H_2$/CO=1:1). The result is shown in Illustration 18, in which the long-term stability in the preliminary experiment without addition of the organic amines OA could be doubled to 160 hrs. At the start of the experiment, the TOF is about 100 hr$^{-1}$ and ends at about 80 hr$^{-1}$. The maximum conversion is about 10% and the selectivity for n-pentanal is constant at over 99%. Higher-boiling products were not detected during this experiment.

Figure 18:
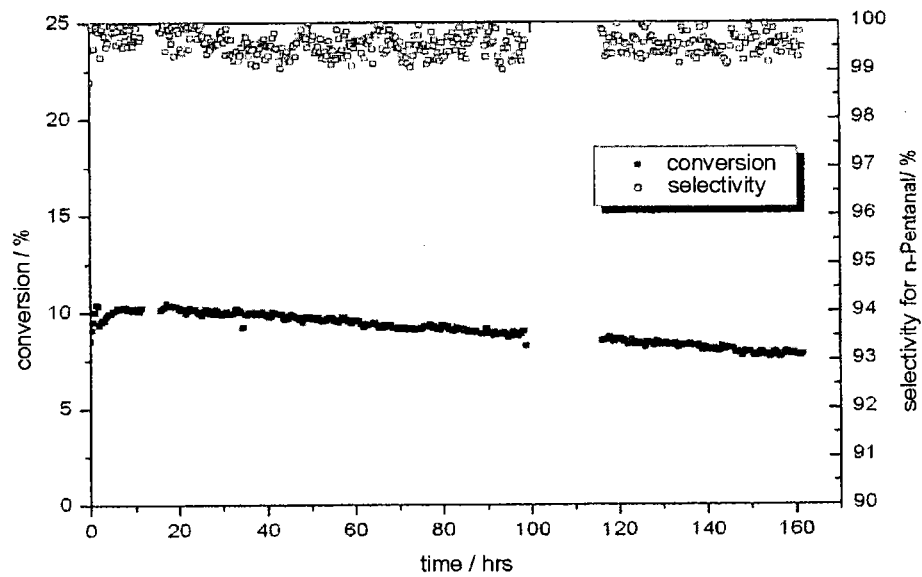
FIG. 18 shows a hydroformylation with water-containing raffinate I with the use of the ligand VIII in the SILP catalyst system.

Illustration 18 Corresponds to FIG. 18

Illustration 18. Hydroformylation with water-containing raffinate I with the use of the ligand VIII in the SILP catalyst system
Experimental conditions: T=80° C., p=1.0 mPa, τ=35 secs, $H_2$:CO=1,
Volume flow$_{raffinate1}$=2.5 ml min$^{-1}$, Volume flow$_{H2}$=Volume flow$_{CO}$=5.6 ml min$^{-1}$, $m_{SILP(Rh-L200)}$=3 g, $m_{Rh}$=0.2%, L/Rh=10, OA/L=1, $α_{IL}$=10 vol. % (IL=[EMIM][NTf$_2$]).

The progression confirms marked stabilization of the catalyst system by use of the amine OA.

Preparation of the Substrate Raffinate I

In order to achieve a higher long-term stability than 160 hrs, raffinate I was dried. During this, the water content of 500 ppm was reduced to at most 20 ppm. In order to reduce continuous water input via the synthesis gas, CO 3.0 was replaced by CO 3.7. Hydrogen 5.0 was again used. In addition, in the preparation of the SILP catalyst system on the basis of Example 1 the organic amine OA was added in the ratio OA/L=2. This preparation of the substrate resulted in a long-term stability of more than 500 hrs (see Illustration 19). After 630 hours of operation the SILP catalyst system was evacuated for 2 hrs. During an operating time of 680 hrs up to the temperature increase, the selectivity for n-pentanal was constantly over 98%. By change in the partial pressure of the raffinate I, the TOF could be raised from 350 hr$^{-1}$ to 1200 hr$^{-1}$, as a result of which it was higher by a factor of 3.5-12 than in the previous experiment. The highest space-time yield (STY), at 0.45 kglcat$^{-1}$ hr$^{-1}$ was achieved at high partial pressures of raffinate I (GHSV=24.8 llcat$^{-1}$ hr$^{-1}$).

Figure 19:
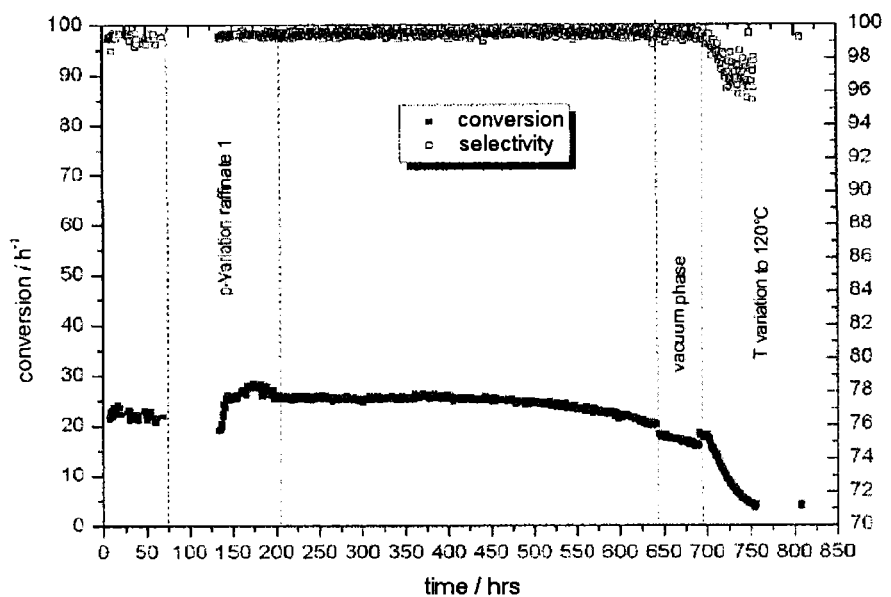
FIG. 19 shows hydroformylation with dried raffinate I with the use of the ligand VIII in the SILP catalyst system.

Illustration 19 Corresponds to FIG. 19

Illustration 19. Hydroformylation with dried raffinate I with the use of the ligand VIII in the SILP catalyst system
Experimental conditions: T=100° C., p=1.0 mPa, τ=15-32 secs, $H_2$:CO=1,
Volume flow$_{raffinate1}$=3.3-20 ml min$^{-1}$, Volume flow$_{H2}$=Volume flow$_{CO}$=3.2-6.0 ml min$^{-1}$, $m_{SILP(Rh-L200)}$=3 g, $m_{Rh}$=0.2%, L/Rh=10, OA/L=2, $α_{IL}$=10 vol. % (IL=[EMIM][NTf$_2$]).

In Illustration 20, the hydroformylation of dried raffinate I with the use of an elevated OA/ligand ratio of 4 is shown. By means of the increased content of organic amine, the long-term stability could be raised to more than 1000 hrs. The selectivity for n-pentanal constantly reached over 98%, while the average conversion was 25%. In comparison to the previous experiment the TOF was at a comparable 400 hr$^{-1}$. Overall therefore, a TON of 436000 was obtained, with an STY of 0.1 kglcat$^{-1}$ hr$^{-1}$. (GHSV=5.0 llcat$^{-1}$ hr$^{-1}$). It was found that a larger quantity of organic amine doubles the long-term stability. After about 900 hrs the activity and selectivity began slowly to fall. This is the longest stable experiment phase of an SILP catalyst system in gas phase hydroformylation so far.

Figure 20:
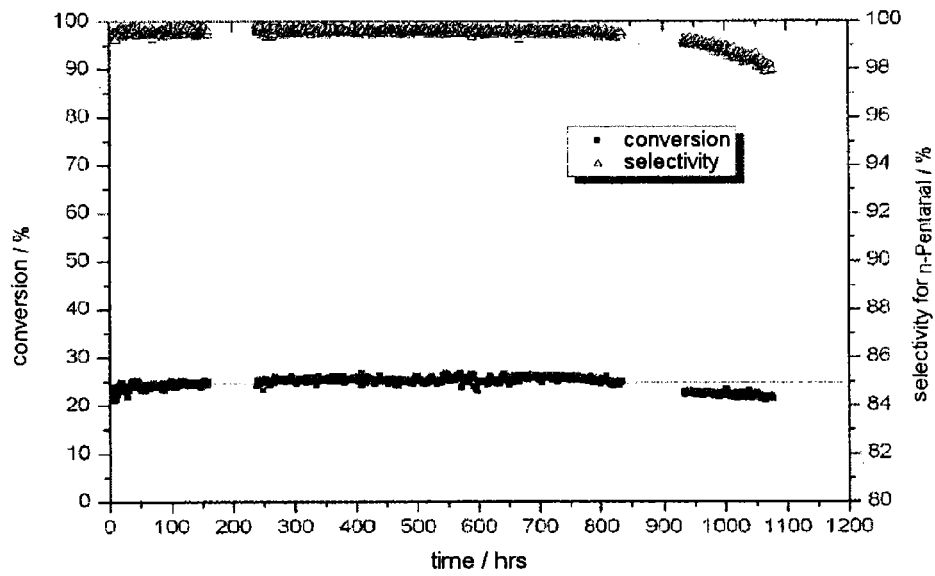
FIG. 20 shows hydroformylation with dried raffinate I and organic amine OA.

Illustration 20 Corresponds to FIG. 20

Illustration 20. Hydroformylation with dried raffinate I and organic amine OA
Experimental conditions: T=100° C., p=1.0 mPa, τ=15-32 secs, $H_2$:CO=1, Volume flow$_{raffinate1}$=16.6 ml min$^{-1}$, Volume flow$_{H2}$=Volume flow$_{CO}$=6.4 ml min$^{-1}$, $m_{SILP(Rh-L200)}$=3 g, $m_{Rh}$=0.2%, L/Rh=10, OA/=4, $α_{IL}$=10 vol. % (IL=[EMIM][NTf$_2$]).

STY Optimization

In order to optimize the space-time yield (abbreviation STY) the overall pressure was varied between 1.0 and 2.5 MPa. The reactor temperature was between 100° C. and 120° C. In Table 8, different parameters, especially temperature, pressure and the partial pressure of raffinate I, were optimized. The residence time was between 22 secs and 28 secs.

The conversion and the STY rose with higher partial pressure of raffinate I (Experiment 1-4). The temperature did not have a major effect, since the activity was only slightly increased with higher temperature (Experiments 2-3). At 2.5 MPa and 120° C. the highest STY at 0.85 kg lcat$^{-1}$ hr$^{-1}$ could be achieved over a period of 10 hrs (Experiment 9). Experiment 7 likewise showed a very high STY of 0.66 kg lcat$^{-1}$ hr$^{-1}$ over 50 hrs.

TABLE 8

STY Optimization

| Expt. | T/° C. | p/MPa | τ/sec | X/% | TOF/hr$^{-1}$ | n/iso sel./% | 2-but./% | trans/cis | STY$_{Butene}$/ kgl$_{cat}^{-1}$hr$^{-1}$ |
|---|---|---|---|---|---|---|---|---|---|
| 1 | 100 | 1.0 | 28 | 23.38 | 384.8 | 99.61 | 25.0 | — | 0.09 |
| 2 | 100 | 1.0 | 28 | 31.14 | 1537.5 | 99.56 | 25.4 | — | 0.35 |
| 3 | 120 | 1.0 | 28 | 31.72 | 1566.1 | 99.14 | 24.9 | — | 0.36 |
| 4 | 120 | 2.0 | 27 | 36.19 | 1786.9 | 99.28 | 29.7 | 2.96 | 0.41 |
| 5 | 120 | 1.5 | 17 | 32.75 | 2695.1 | 99.42 | 29.6 | 2.98 | 0.62 |
| 6 | 120 | 2.0 | 23 | 34.95 | 2875.8 | 99.44 | 28.8 | 3.30 | 0.66 |
| 7 | 120 | 2.0 | 19 | 34.84 | 2867.3 | 99.35 | 29.2 | 3.20 | 0.66 |
| 8 | 120 | 2.0 | 17 | 30.70 | 3536.5 | 99.13 | 29.3 | 3.00 | 0.58 |
| 9 | 120 | 2.5 | 21 | 31.99 | 3572.7 | 98.70 | 30.0 | 2.63 | 0.85 |

Experimental conditions: T = 100-120° C., p = 1.0-2.5 MPa, τ = 17-28 secs, H$_2$:CO = 1.0-2.0, Volume flow$_{raffinate1}$ = 3.3-12.2 ml min$^{-1}$, Volume flow$_{H2}$ = Volume flow$_{CO}$ = 3.5-8.8 ml min$^{-1}$, Volume flow$_{helium}$ = 0-4.5 ml min$^{-1}$. m$_{SILP}$ = 3.0 g, m$_{Rh}$ = 0.2%, L/Rh = 10, OA/L = 4, α$_{IL}$ = 10 vol. % (IL = [EMIM][NTf$_2$]).

Figure 21:
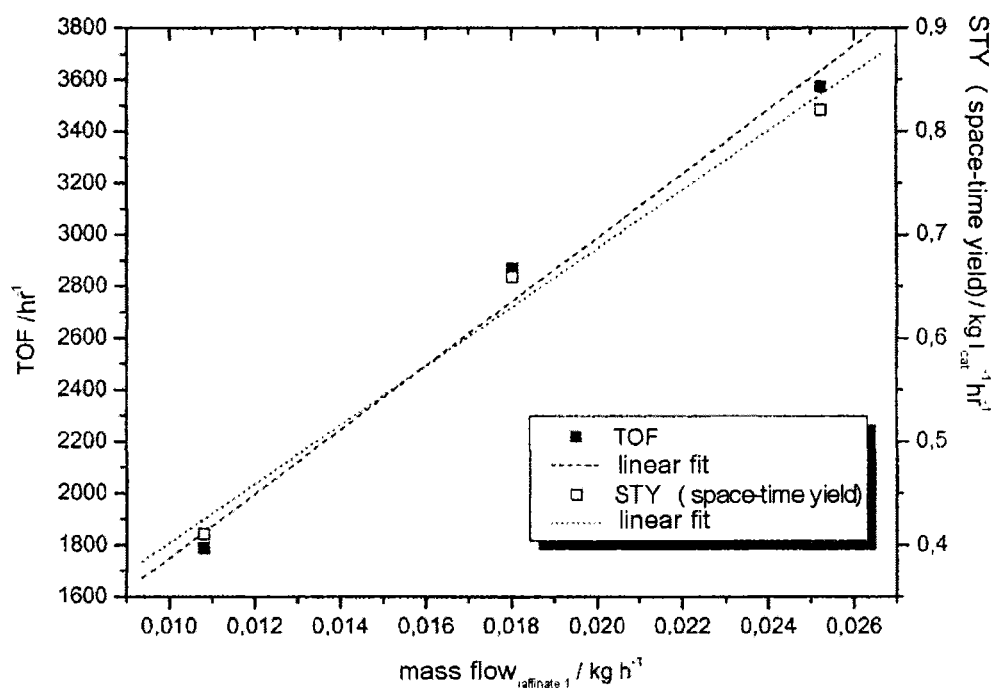
FIG. 21 shows an STY optimization in the raffinate I hydroformylation.

Illustration 21 Corresponds to FIG. 21

Illustration 21. STY optimization in the raffinate I hydroformylation
Experimental conditions: T=100-120° C., p=1.0-2.5 MPa, τ=17-28 secs, H$_2$:CO=1.0-2.0, Volumeflow$_{raffinate1}$=3.3-12.2 ml min$^{-1}$, Volume flow$_{H2}$=Volume flow$_{CO}$=3.5-8.8 ml min$^{-1}$, Volume flow$_{helium}$=0-4.5 ml min$^{-1}$.
m$_{SILP}$=3.0 g, m$_{Rh}$=0.2%, L/Rh=10, OA/=4, α$_{IL}$=10 vol. % (IL=[EMIM][NTf$_2$]).

In Illustration 21, mass flow of raffinate I is plotted against the STY and the TOF respectively. It is evident that with increasing mass flow of raffinate I the TOF and STY rise linearly. At moderate mass flows of raffinate I, the SILP catalyst system already achieves the standard results of a homogeneous catalyst in hydroformylation. Hence high productivity of this system for industrial application is a reality.

In summary, it can be stated that a long-term stable SILP catalyst system in the gas phase hydroformylation of raffinate I can be created through the combination of dried substrates and the use of an organic amine OA in a ratio of OA/L=4, in order to ensure hydroformylation activity for over 1000 hrs.

The invention claimed is:
1. A composition, comprising:
an inert, porous support material,
an ionic liquid,
a group 9 metal,
a phosphorus-comprising organic ligand, and
an organic amine.
2. The composition according to claim 1, wherein the inert, porous support material is selected from the group consisting of aluminium oxide, silicon dioxide, titanium dioxide, zirconium dioxide, silicon carbide, carbon, and any mixture thereof.
3. The composition according to claim 2, wherein the inert, porous support material has
a BET surface area of from 50 to 800 m$^2$/g,
a pore volume of from 0.1 to 2.0 ml/g, and
a mean pore diameter of from 2-80 nm.
4. The composition according to claim 1, wherein the inert, porous support material has a size of from 1-10 mm and a three-dimensional
spherical,
cylindrical,
ellipsoidal, or
polylobular shape, and
the inert, porous support material is obtained by a process comprising adding a binder into the material, wherein the binder is selected from the group consisting of alumina, a ceramic clay, and a colloid.
5. The composition according to claim 1, wherein
an anion of the ionic liquid is selected from the group consisting of: tetrafluoroborate ([BF$_4$]$^-$); hexafluorophosphate ([PF$_6$]$^-$); dicyanamide ([N(CN)$_2$]$^-$); bis(trifluoromethylsulphonyl)imide ([NTf$_2$]$^-$); tricyanomethide ([C(CN)$_3$]$^-$); tetracyanoborate ([B(CN)$_4$]$^-$); a halide selected from the group consisting of Cl$^-$, Br$^-$, F$^-$, and I$^-$; hexafluoroantimonate ([SbF$_6$]$^-$); hexafluoroarsenate ([AsF$_6$]$^-$); sulphate ([SO$_4$]$^{2-}$); tosylate ([C$_7$H$_7$SO$_3$]$^-$); triflate ([CF$_3$SO$_3$]$^-$); nonaflate ([C$_4$F$_9$SO$_3$]$^-$); tris-(pentafluoroethyl) trifluorophosphate ([PF$_3$(C$_2$F$_5$)$_3$]$^-$); thiocyanate ([SCN]$^-$); carbonate ([CO$_3$]$^{2-}$); [R'—COO]$^-$; [R'—SO$_3$]$^-$; [R'PO$_4$R'']$^-$; and [(R'—SO$_2$)2N]$^-$;
wherein R' and R'' each is independently a linear or branched aliphatic or alicyclic residue comprising 1 to 12 carbon atoms, a C$_5$-C$_{18}$ substituted aryl, a C$_5$-C$_{18}$ substituted aryl-C$_1$-C$_6$ alkyl, or a C$_1$-C$_6$ alkyl-C$_5$-C$_{18}$ substituted aryl residue, which is optionally substituted with halogen atoms;
and a cation of the ionic liquid is selected from the group consisting of:
a quaternary ammonium cation of a general formula [NR$^1$R$^2$R$^3$R$^4$]$^+$;
a phosphonium cation of a general formula [PR$^1$R$^2$R$^3$R$^4$]$^+$;
an imidazolium cation of a general formula comprising an imidazole nucleus as shown below

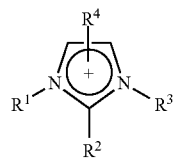

wherein the imidazole nucleus is optionally substituted with at least one group R selected from the group consisting of a C1-C6 alkyl, a C1-C6 alkoxy, a C1-C6 substituted aminoalkyl, a C5-C12 substituted aryl, and a C5-C12 substituted aryl-C1-C6 alkyl group;

a pyridinium cation of a general formula comprising a pyridine nucleus as shown below

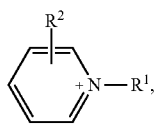

wherein the pyridine nucleus is optionally substituted with at least one group R selected from the group consisting of a C1-C6 alkyl, a C1-C6 alkoxy, a C1-C6 substituted aminoalkyl, a C5-C12 substituted aryl, and a C5-C12 substituted aryl-C1-C6 alkyl group;

a pyrazolium cation of a general formula comprising a pyrazole nucleus as shown below

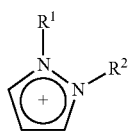

wherein the pyrazole nucleus is optionally substituted with at least one group R selected from the group consisting of a C1-C6 alkyl, a C1-C6 alkoxy, a C1-C6 substituted aminoalkyl, a C5-C12 substituted aryl, and a C5-C12 substituted aryl-C1-C6 alkyl group; and a triazolium cation of a general formula comprising a triazole nucleus as shown below

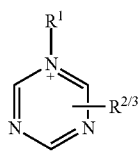

wherein the triazole nucleus is optionally substituted with at least one group R selected from the group consisting of a C1-C6 alkyl, a C1-C6 alkoxy, a C1-C6 substituted aminoalkyl, a C5-C12 substituted aryl, and a C5-C12 substituted aryl-C1-C6 alkyl group, and $R^1$, $R^2$, and $R^3$ each is independently selected from the group consisting of:

hydrogen;

a linear or branched, saturated or unsaturated, aliphatic or alicyclic alkyl group comprising 1 to 20 carbon atoms;

a heteroaryl- or a heteroaryl-C1-C6 alkyl group comprising a heteroaryl residue, 3 to 8 carbon atoms in the heteroaryl residue, and at least one hetero atom selected from the group consisting of N, O and S, wherein the hetero atom is optionally substituted with at least one selected from the group consisting of a C1-C6 alkyl group and a halogen atom; and an aryl or an aryl-C1-C6 alkyl group comprising an aryl residue and 5 to 12 carbon atoms in the aryl residue, wherein the aryl residue is optionally substituted with at least one selected from the group consisting of a C1-C6 alkyl group and a halogen atom.

6. The composition according to claim 1, wherein the ionic liquid is selected from the group consisting of:

1-ethyl-3-methylimidazolium bis(trifluoromethylsulphonyl)imide, 1-butyl-3-methylimidazolium hexafluorophosphate, and 1-butyl-3-methylimidazolium tetrafluoroborate.

7. The composition according to claim 1, wherein the group 9 metal is rhodium.

8. The composition according to claim 1, wherein the phosphorus-comprising organic ligand comprises a phosphorus-oxygen covalent bond or a phosphorus-nitrogen covalent bond.

9. The composition according to claim 8, wherein the phosphorus-comprising organic ligand is selected from the group comprising consisting of:

[6,6-((3,3'-di-tert-butyl-5,5'-dimethoxy-[1,1'-biphenyl]-2,2'-diyl)bis(oxy))bis(dibenzo[d,f][1,3,2]dioxaphosphepine)] of formula VII

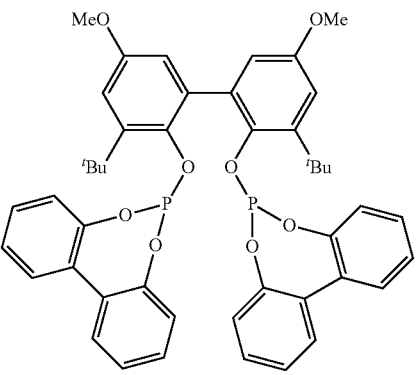

[2,2'4(3,3'-di-tert-butyl-5,5'-dimethoxy-[1,1'-biphenyl]-2,2'-diyl)bis(oxy))bis(4,4,5,5-tetraphenyl-1,3,2-dioxaphospholane)] of formula VIII, and

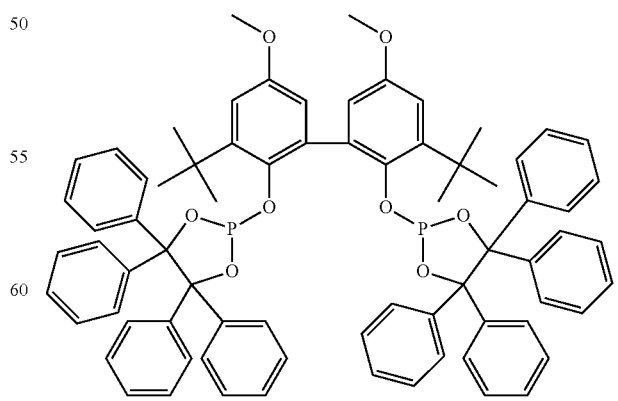

Tris-(2,4-di-tert-butylphenyl) phosphite of formula IX

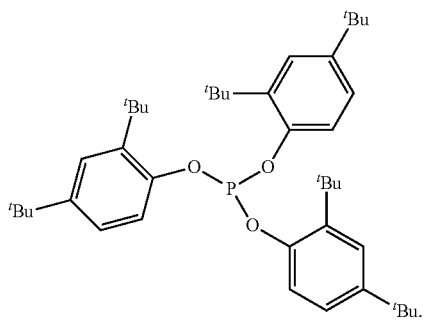

IX

10. The composition according to claim 1, wherein the organic amine is selected from the group consisting of:

an amine of formula X

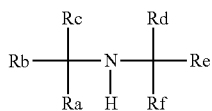

X wherein Ra, Rb, Rc, Rd, Re and Rf each is independently a hydrocarbon residue which is optionally bound to one another, and a tertiary amine selected from the group consisting of an aliphatic amine, an aromatic amine, a cycloaliphatic amine, a heteroaromatic amine, and any mixture thereof.

11. The composition according to claim 10, wherein the organic amine comprises a compound comprising a 2,2,6,6-tetramethylpiperidine unit of formula XI:

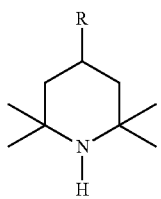

XI wherein R represents an organic residue, H, a hydroxyl group or a halogen.

12. The composition according to claim 11, wherein the organic amine comprises a compound of a formula selected from the group consisting of XIa, XIb, XIc, XId, XIe, XIf, XIg, and XIh:

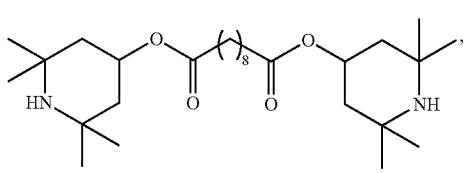

XIa

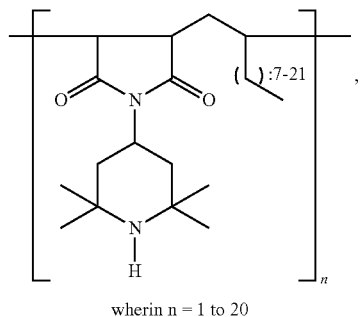

XIb

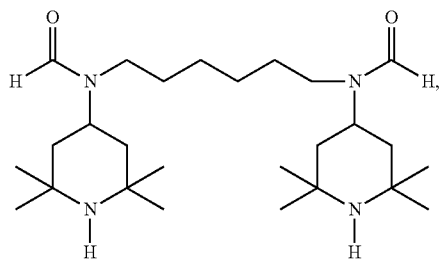

XIc

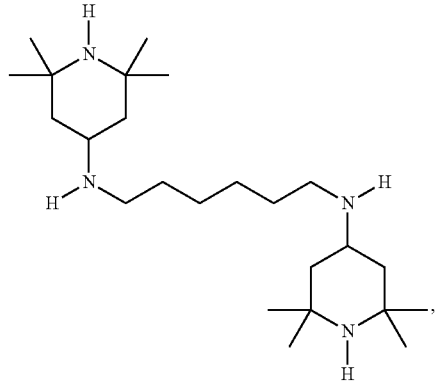

XId

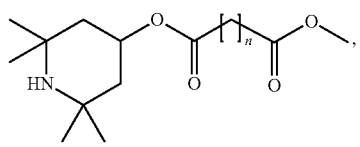

XIe wherein n = 1 to 12

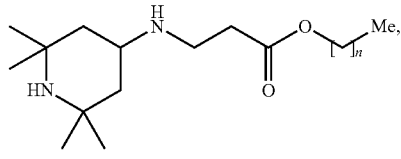

XIf wherein n = 1 to 17

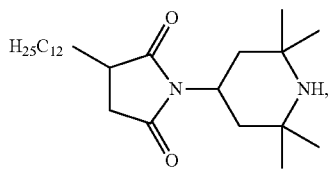

XIg

-continued

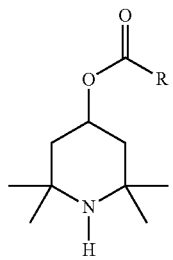

wherein R is a C6 to C20 alkyl.

13. The composition according to claim 10, wherein the organic amine further comprises an organic amine of a formula selected from the group consisting of XIIa, XIIb, XIIc, XIId, XIIe, XIIf, XIIg, XIIh, XIII, and XIIj:

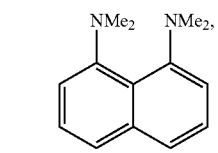
XIIa

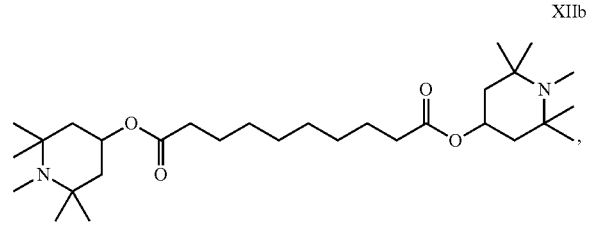
XIIb

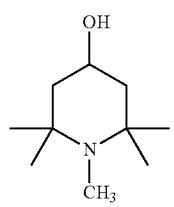
XIIc

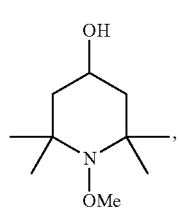
XIId

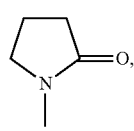
XIIe

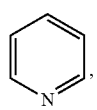
XIIf

-continued

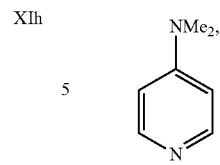
XIIg

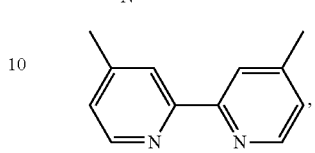
XIIh

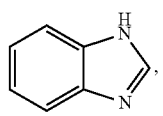
XIIi

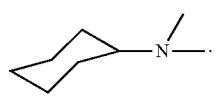
XIIj

14. A multiphase reaction mixture, comprising:
an olefin-comprising hydrocarbon mixture,
a gas mixture comprising carbon monoxide and hydrogen,
an aldehyde, and
the composition according to claim 1.

15. A process for hydroformylation of an olefin-comprising hydrocarbon mixture to an aldehyde, the process comprising:
adjusting a water content of the olefin-comprising hydrocarbon mixture to at most 20 ppm,
adjusting a content of multiply unsaturated compounds in the olefin-comprising hydrocarbon mixture to at most 3000 ppm, and
adding the composition according to claim 1 to the olefin-comprising hydrocarbon mixture, thereby obtaining a reaction mixture, and finally the aldehyde,
wherein
the organic amine is selected from the group consisting of an amine of formula X $$Rb-\underset{Ra}{\overset{Rc}{|}}-\underset{H}{N}-\underset{Rf}{\overset{Rd}{|}}-Re$$
X wherein Ra, Rb, Rc, Rd, Re and Rf each is independently a hydrocarbon residue which is optionally bound to one another,
and a tertiary amine selected from the group consisting of an aliphatic amine, an aromatic amine, a cycloaliphatic amine, a heteroaromatic amine, and any mixture thereof:
the phosphorus-comprising organic ligand comprises a phosphorus-oxygen covalent bond or a phosphorus-nitrogen covalent bond;
the group 9 metal is rhodium;
a molar ratio of the organic amine to the phosphorus-comprising organic ligand is at least 4:1; and
a molar ratio of the phosphorus-comprising organic to rhodium is at least 10:1.

16. The process according to claim 15, wherein the reaction mixture is periodically subjected to a stripping gas treatment for removing the aldehyde.

17. The process according to claim 16, wherein the stripping gas is selected from the group consisting of:
- a mixture of carbon monoxide and hydrogen;
- a mixture of C2-C6 alkanes;
- a mixture of C2-C6 alkanes and C2-C6 alkenes; and
- an inert gas.

18. The process according to claim 15, wherein after obtaining the aldehyde, a part of a gaseous reaction mixture is fed back into the reaction mixture.

19. The process according to claim 15, wherein the olefin-comprising hydrocarbon mixture is selected from the group consisting of:
- ethylene,
- propylene,
- a C4 olefin and a multiply unsaturated compound, and
- a C5 olefin and a multiply unsaturated compound.

* * * * *